United States Patent [19]

Miyashita

[11] Patent Number: 5,241,027
[45] Date of Patent: Aug. 31, 1993

[54] MACROMOLECULAR SPIROPYRAN COMPOUNDS

[75] Inventor: Akira Miyashita, Ageo, Japan

[73] Assignee: Otsuka Kagaku Kabushiki Kaisha, Osaka, Japan

[21] Appl. No.: 768,409

[22] PCT Filed: Feb. 4, 1991

[86] PCT No.: PCT/JP91/00131
§ 371 Date: Oct. 7, 1991
§ 102(e) Date: Oct. 7, 1991

[87] PCT Pub. No.: WO91/12279
PCT Pub. Date: Aug. 22, 1991

[30] Foreign Application Priority Data

Feb. 8, 1990 [JP] Japan ................. 2-30376
Feb. 9, 1990 [JP] Japan ................. 2-30840

[51] Int. Cl.⁵ ............... C08F 226/06; C08F 228/06; C08F 230/00
[52] U.S. Cl. ......................... 526/259; 526/256; 526/243; 526/246; 430/962
[58] Field of Search ............ 526/256, 259; 430/962

[56] References Cited

U.S. PATENT DOCUMENTS

| | | | |
|---|---|---|---|
| 4,485,168 | 11/1984 | Arakawa et al. | 430/345 |
| 4,565,779 | 1/1986 | Arakawa et al. | 430/962 |
| 4,693,962 | 9/1987 | Tamura et al. | 430/345 |
| 4,753,867 | 6/1988 | Arakawa et al. | 430/345 |

FOREIGN PATENT DOCUMENTS

| | | |
|---|---|---|
| 59-122577 | 7/1984 | Japan . |
| 63-308014 | 12/1988 | Japan . |
| 64-29489 | 1/1989 | Japan . |
| 1-152182 | 6/1989 | Japan . |
| 2-78685 | 3/1990 | Japan . |
| 1273746 | 5/1972 | United Kingdom . |

OTHER PUBLICATIONS

Nihon Kagakukai-shi, 1972, vol. 7, Jul. (1972), pp. 1323-1330 abstract.

*Primary Examiner*—Joseph L. Schofer
*Assistant Examiner*—Mark Nagumo
*Attorney, Agent, or Firm*—Armstrong, Westerman, Hattori, McLeland & Naughton

[57] ABSTRACT

A compound comprising 0.001 to 100 mole percent of a structural unit of the formula

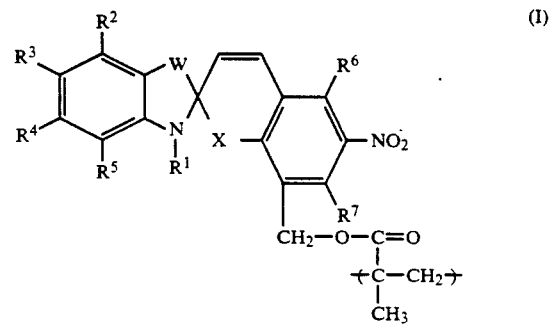

wherein W is $-CMe_2-$ or $-Se-$, $R^1$ is $C_1-C_{20}$ alkyl or aralkyl, $R^2$ to $R^5$ each represents H, $C_1-C_6$ alkyl, etc., $R^6$ and $R^7$ each represents H, $C_1-C_6$ alkyl, etc., X is O or S, provided that when W is $-CMe_2-$, X is S, and 0 to 99.999 mole percent of a structural unit of the formula

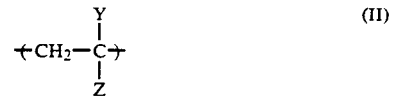

wherein Y is H or Me and Z represents alkoxycarbonyl, phenyl, etc.

28 Claims, 7 Drawing Sheets

MACROMOLECULAR SPIROPYRAN COMPOUNDS

TECHNICAL FIELD

The present invention relates to novel photochromic macromolecular compounds and, more particularly, to macromolecular spiropyran compounds capable of becoming colored upon ultraviolet irradiation or standing in the dark and becoming colorless upon visible light irradiation.

PRIOR ART

Spiropyran derivatives are best known as typical organic compounds reversibly becoming colored or uncolored due to light or heat energy. Specific examples of these derivatives and physical characteristics thereof are summarized, for example, in G. H. Brown: Photochromism (John Wiley & Sons, Inc., 1971).

For practical use as photoresponsive materials, however, the so-far known spiropyran derivatives have drawbacks; for instance (1) colored species or uncolored species, in solutions as well as in macromolecular binders, are lacking in heat stability and therefore immediately return to the uncolored system or colored system, respectively; (2) in the course of repeated color change under the influence of light and heat, the spiropyran derivatives are decomposed or degraded due to side reactions arising from the instability of the metastable system, hence cannot have satisfactory repetition cycles of color change; (3) while, for their use as materials for producing media, they are generally dissolved in macromolecular substances, the spiropyran derivatives generally have poor compatibility with the macromolecular substances, so that the spiropyran derivatives may be exuded from the macromolecular substances or undergo phase separation to give deposits.

The so-called macromolecular spiropyran compounds wherein a spiropyran skeleton is introduced into a polymer chain through chemical bonding are considered to be able to serve as most useful photochromic materials. However, the number of research reports on such compounds is very small as compared with those on low-molecular spiropyran compounds; only a few disclosures are found, for example, in Nippon Kagaku Kaishi, 1323 (1972), J. Polym. Sci. Polym. Chem. Ed., 12, 2511 (1974), Japanese Unexamined Patent Publication (kokai) No. 88895/1978, and Japanese Unexamined Patent Publication No. 76514/1986. The examples disclosed in these are all macromolecular compounds derived by incorporating an indoline- or benzothiazolino-spiropyran compound into a polymer chain through chemical bonding.

A spiropyran compound of the general formula

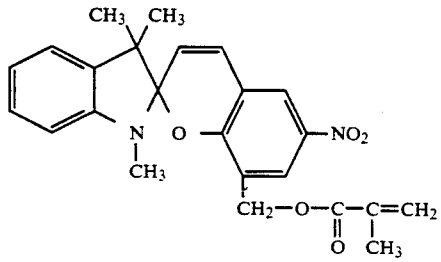

is disclosed in the above-cited Nippon Kagaku Kaishi, 1323 (1972), and the photochromic characteristics of polymers obtained by homopolymerization of the said compound and of polymers obtained by copolymerization of the said compound with styrene or methyl methacrylate have been investigated.

However, in spite of the general idea that high molecular weights resulting from polymerization should result in an increase in the stability of colored species, the colored species of a copolymer of said compound and styrene, for instance, is very unstable, its half-life in benzene being as short as about 1 minute. Thus, at room temperature, it returns to its stable state (becomes colorless) immediately. This is a serious obstacle to its practical use as a photoresponsive material.

DISCLOSURE OF THE INVENTION

It is an object of the invention to provide compounds which obviates the above-mentioned drawbacks of the prior art spiropyran derivatives. In particular, it is an object of the invention to provide compounds showing stable photochromism.

The present inventor made intensive investigations to solve the problems mentioned above and, as a result, found that homopolymers of a polymerizable spirobenzothiopyran or benzoselenazolino-spiropyran compound having a specific structure and copolymers of said compound and a polymerizable vinyl compound can achieve the above objects. This finding has now led to completion of the present invention.

The present invention provides polymers comprising (a) 0.001 to 100 mole percent of a structural unit of the general formula

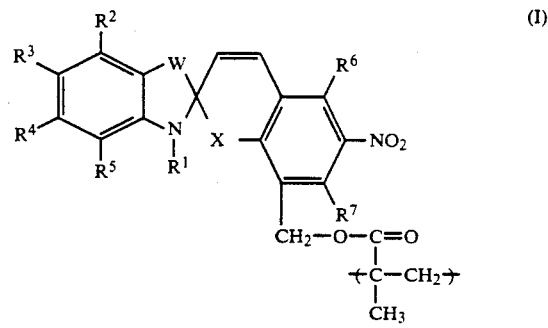

(I)

wherein W is

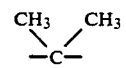

or —Se—, $R^1$ is an alkyl group containing 1 to 20 carbon atoms or an aralkyl group, $R^2$, $R^3$, $R^4$ and $R^5$ are the same or different and each represents a hydrogen atom, an alkyl group containing 1 to 6 carbon atoms, an aryl group, an aralkyl group, an alkoxy group containing 1 to 5 carbon atoms, a halogen atom, a cyano group, a trichloromethyl group, a trifluoromethyl group or a nitro group, $R^6$ and $R^7$ are the same or different and each represents a hydrogen atom, an alkyl group containing 1 to 6 carbon atoms, an aryl group, an aralkyl group, a halogen atom, a cyano group or a nitro group, and X is an oxygen or sulfur atom, with the proviso that X is a sulfur atom when W is

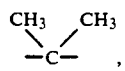

and (b) 0 to 99.999 mole percent of a structural unit of the general formula

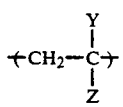

(II)

wherein Y is a hydrogen atom or a methyl group and Z is a carboxyl group, an alkoxycarbonyl group, a cyano group, a carbamoyl group, an N,N-dimethylcarbamoyl group, an acetoxy group, a phenyl group or a methyl phenyl group.

The compounds of the invention show stable photochromism. In the compounds of the invention, a spiropyran skeleton has been introduced into a polymer chain through chemical bonding. As a result, the stability of the spiropyran compounds in the colored state and in the uncolored state is increased and, at the same time, the above-mentioned prior art problem of exudation or deposition of the spiropyrans from macromolecular substances is solved. Thus the compounds of the invention can, by themselves, be formed into photoresponsive films and other media and, as photoresponsive macromolecular compounds, they make it possible to photoreversibly bring out the structure change and/or such performance characteristic as polarity, viscosity or solubility therefrom. Accordingly, the compounds can be expected to be utilizable in such fields as high-density photorecording materials, optical filters, image-forming materials, photosensitive materials, nonlinear optical devices, and conversion of light energy to mechanical energy.

In the spiropyran structural unit of general formula (I) in the macromolecular spiropyran compounds of the present invention, the aralkyl group includes, for example, a phenyl-$C_1$-$C_6$ alkyl group, which may optionally have 1 to 5 (particularly 1, 2 or 3) substituents selected from among $C_1$-$C_6$ alkyl, $C_1$-$C_6$ alkoxy, halogen, cyano, trichloromethyl, trifluoromethyl and nitro on its benzene ring; and the aryl group includes, for example, a phenyl group, which may optionally have 1 to 5 (particularly 1, 2 or 3) substituents each selected from among $C_1$-$C_6$ alkyl, $C_1$-$C_6$ alkoxy, halogen, cyano, trichloromethyl, trifluoromethyl and nitro. The halogen atom includes, for example, a fluorine, chlorine, bromine or iodine atom.

In the structural unit of general formula (II), the alkoxy moiety of the alkoxycarbonyl group represented by Z is, for example, of about 1 to about 8 carbon atoms.

Particularly preferred as the structural unit of general formula (II) are the one in which Y is methyl and Z is methoxycarbonyl, the one in which Y is hydrogen and Z is phenyl, and the like.

In accordance with an embodiment of the invention, polymers are provided which comprise 0.001 to 100 mole percent of a spirobenzothiopyran structural unit of the general formula

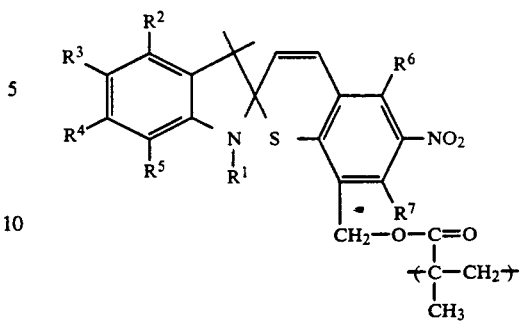

wherein $R^1$, $R^2$, $R^3$, $R^4$, $R^5$, $R^6$ and $R^7$ are as defined above, and 0 to 99.999 mole percent of the structural unit of the foregoing general formula (II).

The above-mentioned macromolecular spirobenzothiopyran compounds of this invention have a number average molecular weight of about $1 \times 10^3$ to about $1 \times 10^6$, preferably about $5 \times 10^3$ to about $3 \times 10^5$, as determined by gel permeation chromatography (GPC) (solvent=tetrahydrofuran, temperature=40° C., based on the standard polystyrene) and a weight average molecular weight of about $1 \times 10^3$ to about $1 \times 10^6$, preferably about $5 \times 10^3$ to $5 \times 10^5$, as determined by the same GPC as mentioned above.

The compounds of the invention may be either homopolymers consisting of the structural unit of the foregoing general formula (I-1) alone or copolymers comprising the structural unit of general formula (I-1) and the structural unit of general formula (II). In such copolymers, it is preferred that the spirothiopyran structural unit of the formula (I-1) be present in said copolymers in an amount of about 0.001 to 50 mole percent, preferably about 0.01 to 25 mole percent, more preferably about 0.1 to 10 mole percent, with the balance accounting for the structural unit of general formula (II), since the desired photochromism cannot be attained when the content of the spirothiopyran structural unit of general formula (I-1) is too small.

The colored species (unstable state) of these compounds have much increased stability and much prolonged life as compared with the so-far known spiropyran derivatives mentioned hereinabove. Thus, the compounds of the present invention which contain the structural unit of the foregoing general formula (I-1), when irradiated with ultraviolet light, shift from colorless (stable state) to colored species (unstable state) and the colored species will not return thermally to the completely uncolored state, hence the colored state is fixed. More specifically, the color of said colored species attenuates to some extent following ultraviolet irradiation but the attenuation is very slow and, after the lapse of several months or more, even the above-mentioned very slow attenuation will not be observed any longer. As a result, the colored state is maintained for a very long period at least of the year order.

Upon visible light irradiation, said colored species become completely colorless. When irradiated again with ultraviolet light, the uncolored species turn to the colored species and the colored state becomes fixed again, as mentioned above.

Furthermore, the compounds of the invention are characterized also in that the maximum absorption wavelength (λmax) of the colored species in the form of films has shifted to the longer wavelength side, i.e., to about 670 to 715 nm, with the absorption edge being close to about 900 nm. Therefore they have high ability to absorb light longer in wavelength than 700 nm, such as light emitted by a semiconductor laser, as well.

Among the structural units represented by the foregoing general formula (I-1), those in which $R^1$ is an alkyl group containing 1 to 20 carbon atoms, $R^2$, $R^3$, $R^4$ and $R^5$ are the same or different and each represents a hydrogen atom, a methyl group, an ethyl group, a phenyl group, a methoxyphenyl group, a methoxy group, an ethoxy group, a fluorine atom, a chlorine atom, a bromine atom, a cyano group or a nitro group, and $R^6$ and $R^7$ are the same or different and each represents a hydrogen atom, a methyl group, an ethyl group, a phenyl group or a naphthyl group, especially those in which $R^1$ is an alkyl group containing 1 to 20 carbon atoms, $R^2$, $R^3$, $R^4$ and $R^5$ are the same or different and each represents a hydrogen atom, a phenyl group, a methoxy group, a chlorine atom, a bromine atom, a cyano group or a nitro group, and $R^6$ and $R^7$ are the same or different and each represents a hydrogen atom, a phenyl group or a naphthyl group, are preferred, and those in which $R^1$ is an alkyl group containing 1 to 18 carbon atoms, $R^2$, $R^3$, $R^4$, $R^5$, $R^6$ and $R^7$ each is a hydrogen atom are more preferable.

In accordance with another embodiment of the invention, there are provided polymers comprising 0.001 to 100 mole percent of a benzoselenazolino-spiropyran structural unit of the general formula

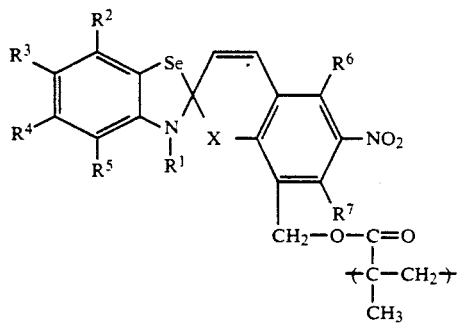

(I-2)

wherein $R^1$, $R^2$, $R^3$, $R^4$, $R^5$, $R^6$, $R^7$ and X are as defined above, and 0 to 99.999 mole percent of the structural unit represented by the foregoing general formula (II).

The above-mentioned macromolecular benzoselenazolinespiropyran compounds of this invention have a number average molecular weight of about $1 \times 10^3$ to about $1 \times 10^6$, preferably about $5 \times 10^3$ to about $3 \times 10^5$, as determined by gel permeation chromatography (GPC) (solvent=tetrahydrofuran, temperature=40° C., based on the standard polystyrene) and a weight average molecular weight of about $1 \times 10^3$ to about $2 \times 10^6$, preferably about $5 \times 10^3$ to about $5 \times 10^5$, as determined by the same GPC as just mentioned above.

The compounds of the invention may be either homopolymers consisting of the structural unit of the foregoing general formula (I-2) alone or copolymers comprising the structural unit of general formula (I-2) and the structural unit of general formula (II). In the case of such copolymers, it is preferred that said spiropyran structural unit of the formula (I-2) be present in said copolymers in an amount of about 0.001 to 50 mole percent, preferably about 0.01 to 25 mole percent, more preferably about 0.1 to 10 mole percent, with the balance accounting for the structural unit of general formula (II), since the above-mentioned desired photochromism cannot be attained when the content of the spiropyran structural unit of general formula (I-2) is too small.

These compounds are characterized in that they are normally (at room temperature) colored, become colorless upon visible light irradiation, and return to the original colored species upon ultraviolet irradiation or heating, thus exhibiting the so-called "negative" photochromism.

More specifically, the compounds become colorless upon visible light irradiation, but the resulting colorless compounds (uncolored species) become gradually colored under the influence of heat. The thermal half-life in that case is very long as compared with the corresponding starting monomers. The above-mentioned uncolored species will not be fully colored and their weakly colored state remains fixed at least at a temperature around room temperature.

The compounds fixed in a semifaded state, when again irradiated with visible light, turn into the uncolored species and, when allowed to stand at a temperature around room temperature, they maintain the semifaded state. Such cycle can be repeated.

Among the structural units represented by the foregoing general formula (I-2), those in which $R^1$ is an alkyl group containing 1 to 20 carbon atoms, $R^2$, $R^3$, $R^4$ and $R^5$ are the same or different and each represents a hydrogen atom, a methyl group, an ethyl group, a phenyl group, a methoxyphenyl group, a methoxy group, ethoxy group, a fluorine atom, a chlorine atom, a bromine atom, a cyano group or a nitro group, and $R^6$ and $R^7$ are the same or different and each represents a hydrogen atom, a methyl group, an ethyl group, a phenyl group or a naphthyl group, in particular those in which $R^1$ is an alkyl group containing 1 to 20 carbon atoms, $R^2$, $R^3$, $R^4$ and $R^5$ are the same or different and each represents a hydrogen atom, a phenyl group, a methoxy group, a chlorine atom, a bromine atom, a cyano group or a nitro group and $R^6$ and $R^7$ are the same or different and each represents a hydrogen atom, a phenyl group or a naphthyl group, are preferred, and those in which $R^1$ is an alkyl group containing 1 to 20 carbon atoms, $R^2$ and $R^5$ each is a hydrogen atom, $R^3$ is a hydrogen atom or an alkoxy group containing 1 to 5 carbon atoms, $R^4$ is a hydrogen atom, an alkyl group containing 1 to 6 carbon atoms or an alkoxy group containing 1 to 5 carbon atoms, $R^6$ and $R^7$ each is a hydrogen atom, and X is an oxygen atom, in particular those in which $R^1$ is a methyl group or an octadecyl group, $R^2$, $R^3$, $R^5$, $R^6$ and $R^7$ each is a hydrogen atom, $R^4$ is a hydrogen atom, a methyl group or a methoxy group, and X is an oxygen atom, are more preferred.

The compounds of this invention are produced by homopolymerizing a spiropyran compound of the general formula

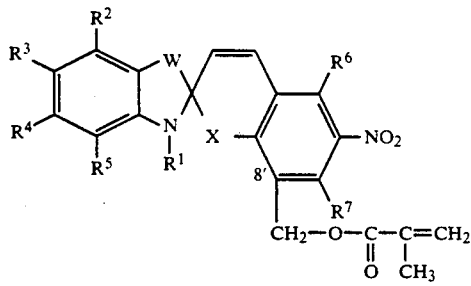

(Ia)

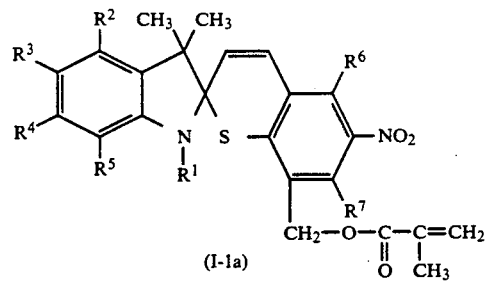

(I-1a)

wherein W, $R^1$, $R^2$, $R^3$, $R^4$, $R^5$, $R^6$, $R^7$ and X are as defined above, which formula corresponds to the spiropyran structural unit in the foregoing general formula (I), or copolymerizing said spiropyran compound with a polymerizable vinyl monomer of the general formula

(IIa)

wherein Y and Z are as defined above, which formula corresponds to the structural unit of general formula (II).

The vinyl monomers of the above general formula (IIa) are all known. Thus, for example, methacrylic acid, acrylic acid, $C_1$-$C_8$ alkyl esters of methacrylic acid or acrylic acid, acrylonitrile, acrylamide, N,N-dimethylacrylamide, vinyl acetate, styrene, α-methylstyrene, vinyltoluene, and the like are suitably used.

Among the compounds of general formula (Ia), those compounds in which W is

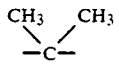

can be readily produced, as illustrated below by the reaction scheme 1, by reacting a 2-methylene-3,3-dimethylindolenine derivative of the general formula (IV-1) with a 3-methacryloxymethyl-5-nitrothiosalicylaldehyde derivative of the general formula (III), with heating.

Reaction Scheme 1

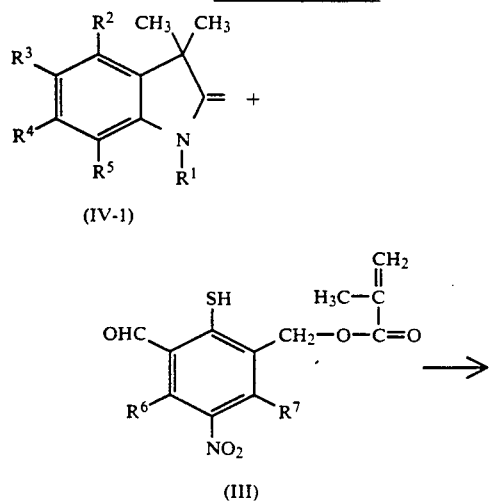

-continued
Reaction Scheme 1

In the above formula $R^1$, $R^2$, $R^3$, $R^4$, $R^5$, $R^6$, and $R^7$ are as defined above.

The 3-methacryloxymethyl-5-nitrothiosalicylaldehyde derivative of general formula (III), which is used as a starting material, can be produced, for example, in the following manner. Thus, a salicylaldehyde derivative of the general formula (V)

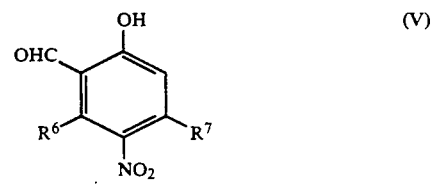

(V)

wherein $R^6$ and $R^7$ are as defined above, is reacted with about 5 to 20 moles, per mole of the compound (V), of chloromethyl methyl ether in the presence of aluminum chloride at about room temperature to about 70° C. for 2 to 25 hours, to give a 3-chloromethyl-5-nitrosalicylaldehyde derivative of the general formula (VI)

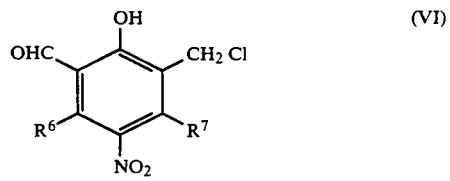

(VI)

wherein $R^6$ and $R^7$ are as defined above. Then, the compound of general formula (VI) is reacted with about 1 to 2 moles, per mole of the compound (VI), of silver methacrylate in a solvent, such as toluene, at about 100° to 120° C. for 2 to 20 hours, to give a 3-methacryloxymethyl-5-nitrosalicylaldehyde derivative of the general formula (VII)

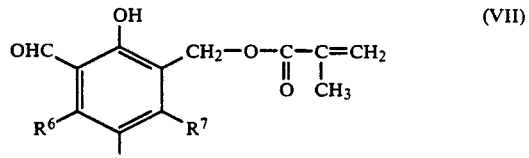

(VII)

wherein $R^6$ and $R^7$ are as defined above. The compound of general formula (VII) is then reacted with N,N-dimethylthiocarbamoyl chloride as described, for example, in Japanese Unexamined Patent Publication (kokai) No. 54388/1985, to give an 2-O-(N,N-dimethylthiocarbamoyl)benzaldehyde derivative of the general formula (VIII)

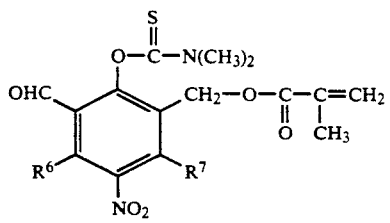

wherein $R^6$ and $R^7$ are as defined above. This is isomerized by heating in a solvent, such as ethanol or toluene, at a refluxing temperature for about 2 to 24 hours, to give a 2-S-(N,N-dimethylthiocarbamoyl)benzaldehyde derivative of the general formula (IX)

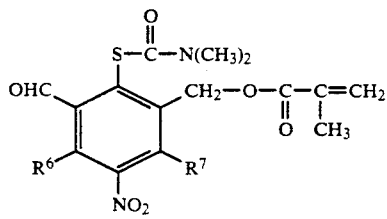

wherein $R^6$ and $R^7$ are as defined above. The subsequent alkali hydrolysis of the compound (IX) in methanol at room temperature gives the corresponding compound of general formula (III).

On the other hand, the 2-methylene-3,3-dimethylindolenine derivative of general formula (IV-1) can be produced by reacting the corresponding 2,3,3-trimethylindolenine derivative with an at least equimolar amount, preferably 1.05 to 1.5 moles per mole of said derivative, of a compound of the general formula $R^1I$ (in which $R^1$ is as defined above) at about 50° to 120° C. for about 0.5 to 20 hours, then adding an aqueous alkali hydroxide solution to the resulting 1-substituted-2,3,3-trimethylindolenium iodide and heating the mixture at room temperature to 80° C. for about 0.3 to 18 hours. The above-mentioned 2,3,3-trimethylindolenine derivatives are either known compounds described in Helv. Chim. Acta, 23, 2471 (1940), Japanese Examined Patent Publication (kokoku) No. 58654/1983, Japanese Unexamined Patent Publication (kokai) No. 232461/1987, Japanese Examined Patent Publication No. 21780/1987 and Japanese Unexamined Patent Publication No. 267783/1988, among others, or can be produced by the methods described in these publications.

The above-mentioned reaction between the 3-methacryloxymethyl-5-nitrothiosalicylaldehyde derivative of general formula (III) and the 2-methylene-3,3-dimethyl indolenine derivative of general formula (IV-1) can be carried out by dissolving both of the reactants in an appropriate solvent and heating the solution at a temperature between room temperature and about the boiling point of the solvent for about 1 to 20 hours. The compound of general formula (III) is preferably used in an amount of about 0.9 to about 1.1 moles per mole of the compound of general formula (IV-1). The solvent mentioned above may be any of those solvent which can dissolve both the compound of general formula (III) and the compound of general formula (IV-1), for example ketones, such as acetone and methyl ethyl ketone, esters, such as ethyl acetate and butyl acetate, halogenated hydrocarbons, such as dichloromethane, dichloroethane and chloroform, and dimethylformamide.

The above-mentioned method of producing the compound of general formula (III) and of the compound of general formula (IV-1) and the method of producing the compound of general formula (I-1a) by reacting the compound of general formula (III) and the compound of general formula (IV-1) will be detailedly described later in Reference Examples 1 to 7.

On the other hand, among the monomers represented by the foregoing general formula (Ia), those compounds in which W is —Se— can be readily produced, as illustrated below by the reaction scheme 2, by subjecting a benzoselenazolium derivative of the general formula (IV-2) and a 3-methacryloxymethyl-5-nitrosalicylaldehyde derivative of the general formula (III') to condensation reaction in the presence of an amine catalyst.

Reaction Scheme 2

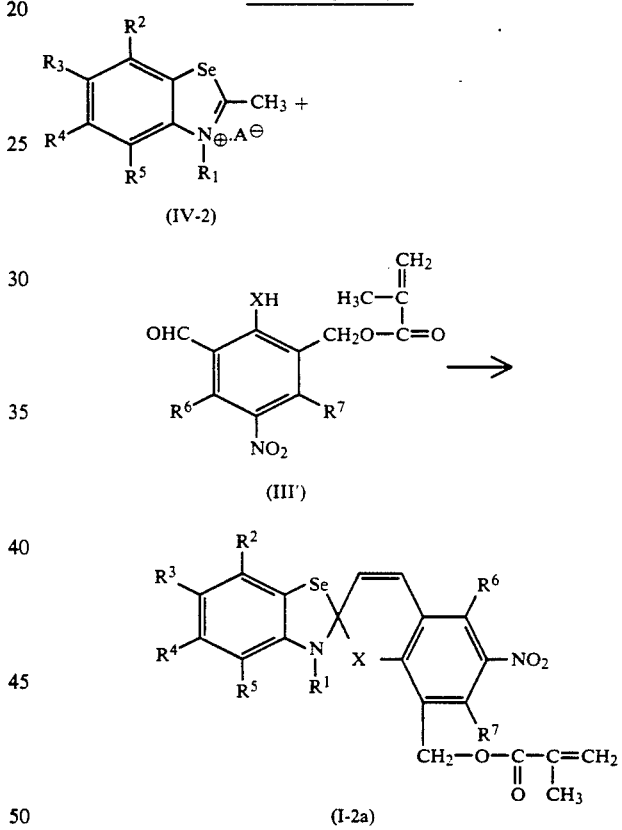

In the above formula, $R^1$, $R^2$, $R^3$, $R^4$, $R^5$, $R^6$, $R^7$ and X are as defined above, and A is a halogen atom, such as a chlorine, bromine or iodine atom, or an $R^8SO_3$ group or the like. $R^8$ is a lower alkyl group, such as methyl or ethyl, or a phenyl group which may optionally have a halogen atom, such as fluorine, chlorine, bromine or iodine, or a $C_1$-$C_4$ alkyl group as a substituent.

The 3-methacryloxymethyl-5-nitrosalicylaldehyde derivative of general formula (III'), which is used as a starting material, can be produced in the same manner as the production of the compound of general formula (III) in the reaction scheme 1 shown hereinabove.

The benzoselenazolium derivative of general formula (IV-2) can be produced by reacting the corresponding 2-methylbenzoselenazole derivative with at least an equimolar amount, preferably 1.05 to 1.5 moles per mole thereof, of a compound of the general formula R¹A (in which R¹ and A are as defined above) at about 50° to 120° C. for about 0.1 to 5 days. The above-mentioned 2-methylbenzoselenazole derivatives are either known compounds described, for example in J. Amer. Chem. Soc., 68, 1536 (1946) or British Patent No. 1411957 (1975) or can be produced by the methods described in the above-cited publications.

The above-mentioned reaction between the 3-methacryloxymethyl-5-nitrosalicylaldehyde derivative of general formula (III') and the benzoselenazole derivative of general formula (IV-2) can be carried out by dissolving both of the reactants in an appropriate solvent, adding an amine catalyst dropwise in small portions to the solution at a temperature between room temperature and about the boiling point of the solvent and heating the resulting mixture for about 1 to 24 hours. The compound of general formula (III') is preferably used in an amount of about 0.9 to 1.1 moles per mole of the compound of general formula (IV-2). As regards the solvent mentioned above, any of those organic solvents which can dissolve the compound of general formula (III') and the compound of general formula (IV-2) can be used, for example methanol, ketones, such as acetone and methyl ethyl ketone, esters, such as ethyl acetate and butyl acetate, halogenated hydrocarbons, such as dichloromethane, dichloroethane and chloroform, and dimethylformamide. Usable as the above-mentioned amine catalyst are piperidine, morpholine, triethylamine, pyridine, lutidine, 1,4-diazabicyclo[2,2,2]octane, 1,5-diazabicyclo[4,3,0]nonene,1,8-diazabicyclo[5,4,0]undecene, etc. The catalyst may be used in an amount of about 1 to 10 moles per mole of the compound of general formula (IV-2).

The method of homopolymerizing the thus-obtained spirobenzothiopyran compound or benzoselenazolinespiropyran compound of general formula (Ia) and the method of copolymerizing said compound with a vinyl monomer of general formula (IIa) are described in the following.

The above-mentioned homopolymerization and copolymerization can be carried out in the same manner and under the same conditions as the synthetic reactions for conventional vinyl resins and the like. Thus, for example, the monomeric compound of general formula (Ia) is dissolved, either alone or together with the compound of general formula (IIa), in an organic solvent and heating the solution in the presence of a radical polymerization initiator at a temperature of about 50° to 100° C. with stirring. The reaction time may be about 0.1 to 100 hours when the monomer of general formula (I-1a) is used, or generally about 1 to 50 hours when the monomer of general formula (I-2a) is used. Usable as the organic solvent are those which are inert to the monomer(s) used and the product macromolecular compound, for example polar organic solvents of the amide type, such as N,N-dimethylformamide, ether solvents, such as diethyl ether and tetrahydrofuran, hydrocarbon solvents, such as toluene, ester solvents, such as ethyl acetate and butyl acetate, ketone solvents, such as acetone and methyl isobutyl ketone, etc. Among these, hydrocarbon solvents, such as toluene, are preferred when the monomer of general formula (I-1a) is used while polar organic solvents of the amide type, such as N,N-dimethylformamide are preferred when the monomer of general formula (I-2a) is used. The radical initiator may be any of those in conventional use and includes, as typical examples, peroxides such as benzoyl peroxide, di-t-butyl peroxide and t-butyl peroxy-2-ethylhexanoate, and azo compounds such a azobisisobutyronitrile and azobisdimethylvaleronitrile. It is also possible to conduct the polymerization under the same conditions as mentioned above using a Grignard reagent, such as phenylmagnesium bromide.

In cases where the compound of this invention is a copolymer comprising the constituent unit of general formula (I) and the constituent unit of general formula (II), the proportions of both constituent units in the copolymer (copolymerization ratio) is determined by such factors as the charge ratio between the spiropyran compound of general formula (Ia) and the vinyl compound of general formula (IIa), the method of polymerization and the like. Therefore, if the relevant relationship is determined in advance with such factors as parameters, the copolymer can be readily produced with a desired copolymerization ratio.

The thus-produced macromolecular spirobenzopyran compound of this invention can be isolated by a known method conventionally used. For example, a poor solvent, such as methanol or ether is added dropwise to the reaction mixture after completion of the polymerization reaction mentioned above, to cause precipitation of said compound as a solid. Said solid can be collected by filtration, for instance.

The following examples are further illustrative of the present invention.

In each figure, the curve (1) is the spectrum before ultraviolet light irradiation, (2) is the spectrum immediately after completion of ultraviolet light irradiation, and (3) is the spectrum at the time when, after gradual fading following ultraviolet light irradiation, any further color density decrease is no more observable, namely at the time when fixation of the colored species has been achieved.

Figure 5:
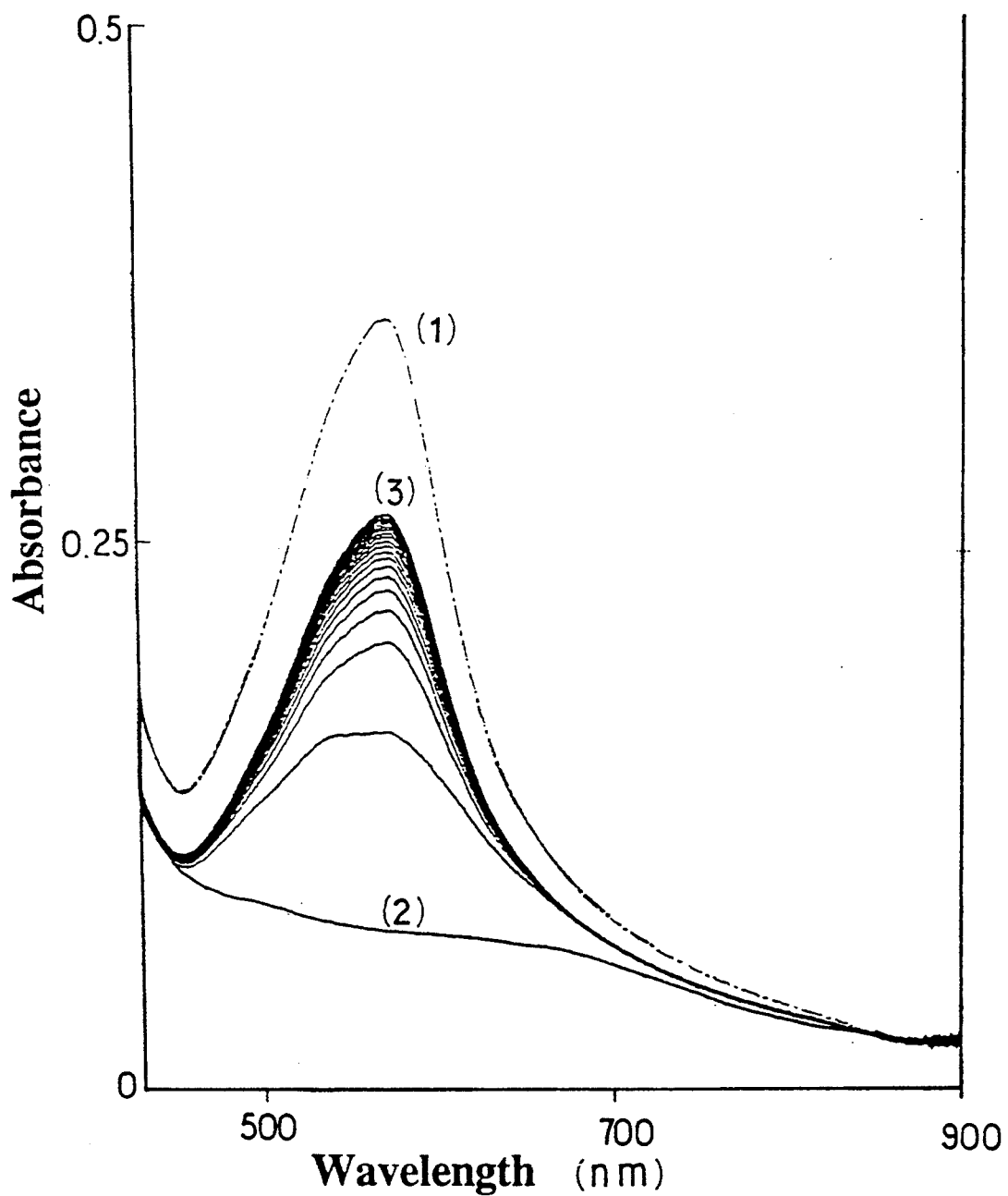

FIG. 5 shows visible light absorption spectra at room temperature of the film obtained in Example 8.

Figure 6:
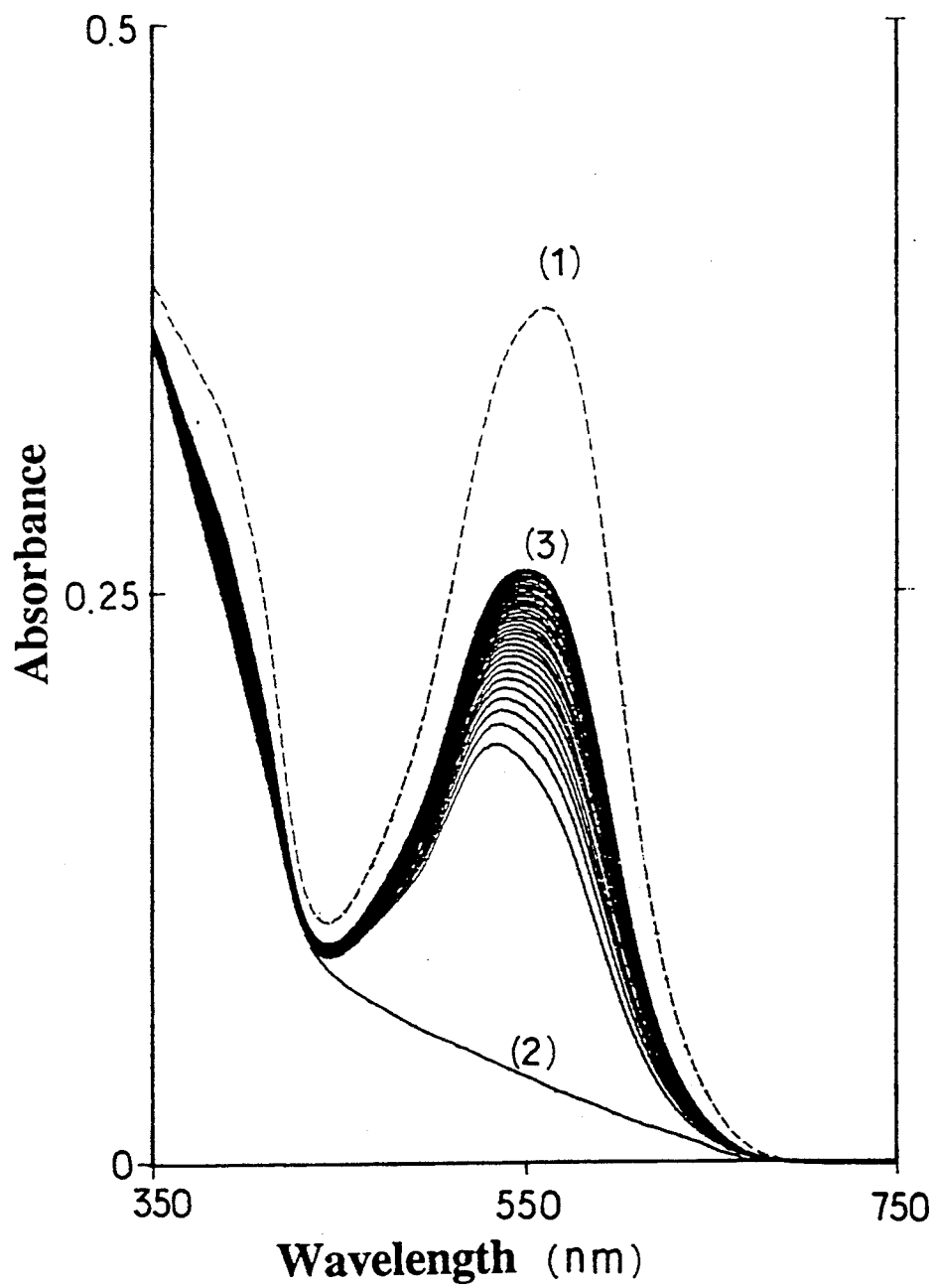

FIG. 6 shows visible light absorption spectra at room temperature of the film obtained in Example 11.

Figure 7:
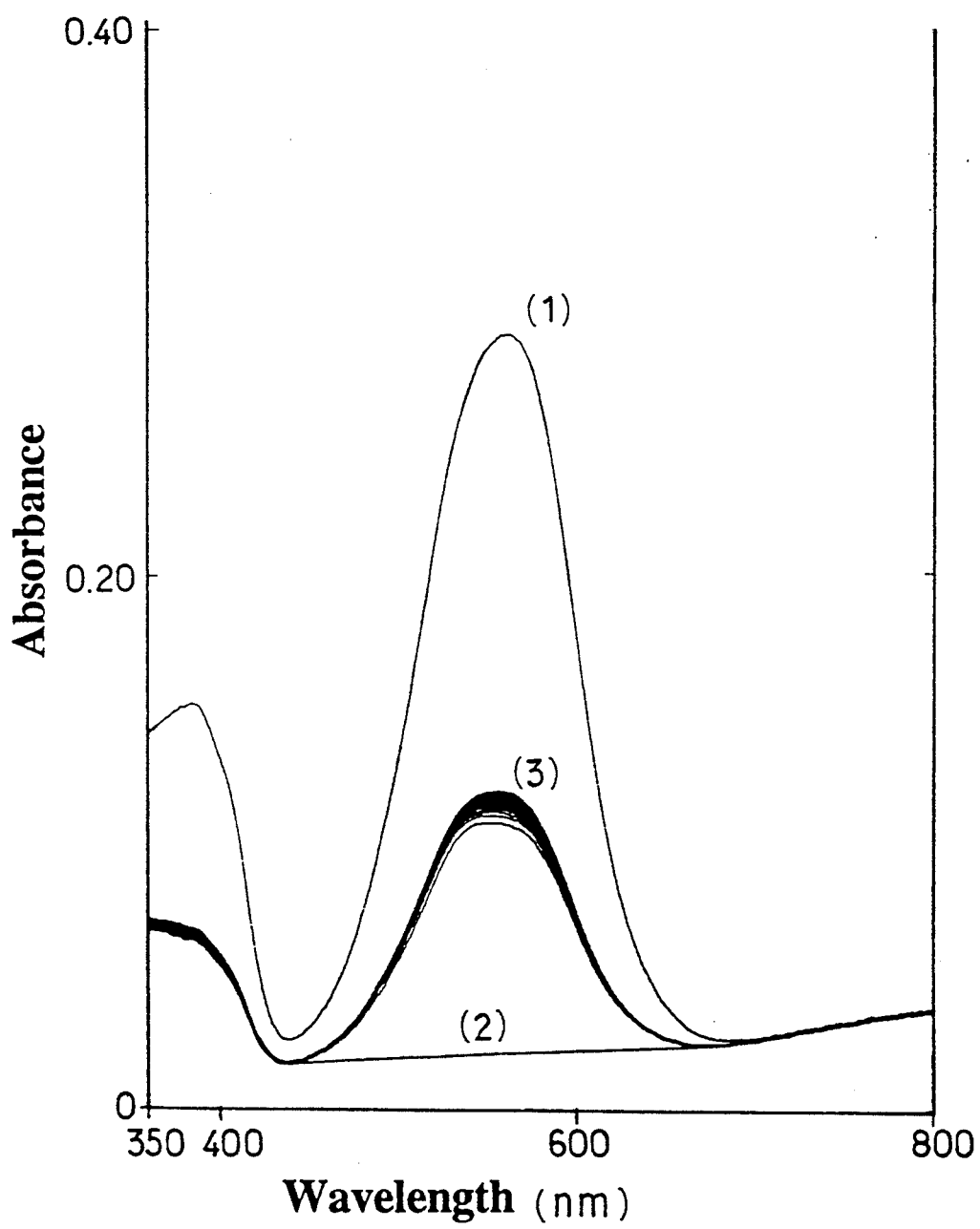

FIG. 7 shows visible light absorption spectra at room temperature of the film obtained in Example 13.

In each of FIGS. 5 to 7, (1) is the spectrum just after film manufacture, (2) is the spectrum immediately after completion of visible light irradiation, and (3) is the spectrum at the time when, after gradual coloration following visible light irradiation, any further color density increase is eventually no more observable (fixation of the uncolored species has been achieved).

Production example for spirobenzothiopyran compounds of the foregoing general formula (I-1a) are shown in Reference Examples 1 to 7. Production examples for benzoselenazolino-spiropyran compounds of general formula (I-2a) are shown in Reference Examples 8 to 19.

REFERENCE EXAMPLE 1

Aluminum chloride (80 g) was added to an ice bath-cooled mixture of 20.0 g of 5-nitrosalicylaldehyde and 200 ml of chloromethyl methyl ether, and the reaction was carried out at room temperature for 1 hour and then at 63° C. for 17 hours. The reaction mixture was cooled on an ice bath, and then 300 ml of ice water was added, and the resultant white precipitate was collected by filtration and recrystallized from hexane to give 18.6 g of 3-chloromethyl-5-nitrosalicylaldehyde (yield 72%).

$^1$H-NMR (CDCl$_3$); δ ppm 4.7 (s, 2H, —CH$_2$—), 8.5 (s, 2H, ArH), 10.0 (s, 1H, CHO), 12.1 (s, 1H, OH).

REFERENCE EXAMPLE 2

A mixture of 10.0 g of 3-chloromethyl-5-nitrosalicylaldehyde and 14.5 g of silver methacrylate in 200 ml of toluene was heated with stirring at 120° C. for 18 hours. The reaction mixture was filtered, and the solution obtained was concentrated under reduced pressure to give 12.5 g of 3-methacryloxymethyl-5-nitrosalicylaldehyde (yield 96%).

$^1$H-NMR (CDCl$_3$); δ ppm 2.0 (d, 3H, CH$_3$), 5.3 (s, 2H, —CH$_2$—), 5.7 (m, 1H, vinyl), 6.2 (m, 1H, vinyl), 8.5 (s, 2H, ArH), 10.0 (s, 1H, CHO), 12.0 (br s, 1H, OH).

IR (KBr); 2950, 1705, 1660, 1600, 1520, 1345 cm$^{-1}$.

REFERENCE EXAMPLE 3

3-Methacryloxymethyl-5-nitrosalicylaldehyde (13.8 g) and 11.2 g of 1,4-diazabicyclo[2,2,2]octane were dissolved in 300 ml of dimethylformamide, and the solution was heated at 50° C. To this was added gradually a solution of 12.9 g of N,N-dimethylthiocarbamoyl chloride in 50 ml of dimethylformamide, and then the whole mixture was heated at 50° C. for 2 hours. The reaction mixture was extracted with ethyl acetate, and the extract was washed with a saturated aqueous solution of sodium chloride and concentrated under reduced pressure to give 17.6 g of 2-O-(N,N-dimethylthiocarbamoyl)-3-methacryloxymethyl-5-nitrobenzaldehyde (crude product yield 96%).

$^1$H-NMR (CDCl$_3$); δ ppm 2.0 (m, 3H, CH$_3$), 3.5 (d, 6H, N—CH$_3$), 5.3 (d, 2H, —CH$_2$—), 5.7 (m, 1H, vinyl), 6.2 (m, 1H, vinyl), 8.6 (d, 1H, ArH), 8.7 (d, 1H, ArH), 10.0 (s, 1H, CHO).

REFERENCE EXAMPLE 4

A mixture of 12.6 g of 2-O-(N,N-dimethylthiocarbamoyl)-3-methacryloxymethyl-5-nitrobenzaldehyde and 100 ml of ethanol was heated under reflux for 21 hours. The reaction mixture was concentrated under reduced pressure, and the residue obtained was dried under reduced pressure and then purified on a silica gel column to give 10.7 g of 2-S-(N,N-dimethylthiocarbamoyl)-3-methacryloxymethyl-5-nitrobenzaldehyde (yield 85%).

$^1$H-NMR (CDCl$_3$) δ ppm 2.0 (s, 3H, CH$_3$), 3.1 (d, 6H, N—CH$_3$), 5.5 (s, 2H, —CH$_2$—), 5.7 (m, 1H, vinyl), 6.2 (m, 1H, vinyl), 8.6 (d, 1H, ArH), 8.7 (d, 1H, ArH), 10.3 (s, 1H, CHO).

IR (KBr); 1720, 1690, 1660, 1535, 1345 cm$^{-1}$.

REFERENCE EXAMPLE 5

To a mixed solution composed of 14.1 g of 2-S-(N,N-dimethylthiocarbamoyl)-3-methacryloxymethyl-5-nitrobenzaldehyde and 200 ml of methanol was added dropwise 140 ml of 0.64N aqueous sodium hydroxide solution at room temperature. Then, the reaction mixture was acidified to pH 2 by adding 380 ml of 0.488N hydrochloric acid. Thereafter the mixture was concentrated under reduced pressure. The residue was extracted with ether, and the extract was washed with water and concentrated under reduced pressure to give 9.79 g of 3-methacryloxymethyl-5-nitrothiosalicylaldehyde as orange-colored crystals (yield 87%).

$^1$H-NMR (CDCl$_3$); δ ppm 2.0 (m, 3H, CH$_3$), 5.3 (s, 2H, —CH$_2$—), 5.7 (m, 1H, vinyl), 6.2 (m, 1H, vinyl), 8.4 (m, 2H, ArH), 10.1 (s, 1H, CHO).

REFERENCE EXAMPLE 6

Methyl iodide (15.9 g) was added to a solution of 16.0 g of 2,3,3-trimethylindolenine in 100 ml of chloroform, and the mixture was heated in an autoclave at 80° C. for 21 hours. The resultant precipitate was isolated by filtration, whereby 27.5 g of 1,2,3,3-tetramethylindolenium iodide was obtained as white crystals. To the crystals was added 270 ml of 10N aqueous potassium hydroxide solution under a nitrogen atmosphere. The mixture was heated at 50° C. for 2.5 hours. The reaction mixture was then extracted with ether, and the extract was dried over magnesium sulfate and then concentrated under reduced pressure to give 14.1 g of 2-methylene-1,3,3-trimethylindoline (yield 81%).

$^1$H-NMR (CDCl$_3$); δ ppm 1.3 (s, 6H, CH$_3$), 3.0 (s, 3H, N—CH$_3$), 6.5–7.0 (dd, 2H, vinyl), 7.0–7.2 (m, 4H, ArH).

REFERENCE EXAMPLE 7

3-Methacryloxymethyl-5-nitrothiosalicylaldehyde (14.1 g) and 8.7 g of 2-methylene-1,3,3-trimethylindoline were dissolved in 120 ml of 2-butanone and the solution was heated under reflux in a nitrogen atmosphere for 20 hours. The reaction mixture was concentrated under reduced pressure and the residue was purified on a silica gel column to give 15.9 g of 8'-methacryloxymethyl-6'-nitro-1,3,3-trimethylspiro[indoline-2,2'(2'H)-1'-benzothiopyran] as light yellow crystals (yield 73%).

$^1$H-NMR (CDCl$_3$); δ ppm 1.24 (s, 3H, CH$_3$), 1.39 (s, 3H, CH$_3$), 1.97 (d, 3H, CH$_3$), 2.67 (s, 3H, N—CH$_3$), 5.15 (dd, 2H, CH$_2$), 5.62 (t, 1H, vinyl), 6.05 (d, 1H, thiopyran), 6.16 (s, 1H, vinyl), 6.51 (d, 1H, thiopyran), 6.65 (t, 1H, indoline), 6.96 (d, 1H, indoline), 7.06 (d, 1H, indoline), 7.17 (t, 1H, indoline), 8.02 (d, 1H, benzothiopyran), 8.08 (d, 1H, benzothiopyran).

EXAMPLE 1

A 979-mg portion (2.25 mmol) of the 8'-methacryloxymethyl-6'-nitro-1,3,3-trimethylspiro[indoline-2,2'(2'H)-1'-benzothiopyran] obtained in Reference Example 7 was dissolved in 30 ml of toluene and 2.30 g (23.0 mmol) of methyl methacrylate. In a nitrogen atmosphere and in the dark, 18.2 mg (0.11 mmol) of α,α'-azobisisobutyronitrile was added to the solution and the polymerization reaction was conducted at 85° C. for 125 hours. The thus-obtained yellow reaction mixture was added dropwise to 500 ml of methanol, whereupon a yellow polymer precipitated out. The precipitate was separated using a glass filter and dried, whereby 1.90 g of a light yellow polymer was obtained.

Based on the physical characteristics described below, this product was identified as a copolymer composed of the starting spirothiopyran compound and methyl methacrylate. Infrared absorption spectrometry (IR analysis) revealed the presence of absorptions due to a nitro group (1522 cm$^{-1}$, 1388 cm$^{-1}$) in addition to a strong absorption due to an ester carbonyl (1732 cm$^{-1}$). GPC (solvent=tetrahydrofuran, temperature=40° C., based on the standard polystyrene; in the subsequent examples, the same shall apply) of this product gave a single peak, the number average molecular weight Mn being 2.66×10$^4$ and the weight average molecular weight Mw being $4.21 \times 10^4$. The elemental analysis data were: C 59.48%, H 7.15% and N 1.56%. Based on said data, the content of the spirothiopyran unit corresponding to general formula (I-1) was calculated to be 5.5 mole percent.

A 10-mg portion of this polymer was dissolved in 2 ml of benzene, and the solution was cast onto a quartz plate, whereby a light-yellow film was obtained. This film was irradiated with ultraviolet rays about 350 nm in wavelength for 1 minute using an ultrahigh pressure mercury lamp (Ushio USH-500D) and an ultraviolet band pass filter (Kenko U-350), whereupon it turned green, with an absorption maximum wavelength λmax of 670 nm. The absorption edge extended to about 900 nm. At 23° C., this green film did not become completely uncolored but maintained a colored state with complete fixation at a colored species fixation percentage of 53%.

The "colored species fixation percentage" as so termed herein is defined as follows (the same shall apply in the subsequent examples and comparative examples):

Colored species fixation percentage (%) =

$$\frac{\begin{pmatrix}\text{Absorbance in} \\ \text{fixed state}\end{pmatrix} - \begin{pmatrix}\text{Absorbance in} \\ \text{uncolored state}\end{pmatrix}}{\begin{pmatrix}\text{Maximum} \\ \text{absorbance}\end{pmatrix} - \begin{pmatrix}\text{Absorbance in} \\ \text{uncolored state}\end{pmatrix}} \times 100$$

In the above expression, the "absorbance in fixed state" means the absorbance at λmax in a state wherein the decrease in absorbance is substantially unobservable any more generally in the course of about 24 hours of visible light absorption spectrum measurement, although the measurement period may vary depending on the sample to be tested. The "absorbance in uncolored state" means the absorbance at the above-mentioned λmax as measured in an uncolored state resulting from irradiation of the film immediately after its manufacture with visible rays longer than 500 nm in wavelength.

Figure 1:
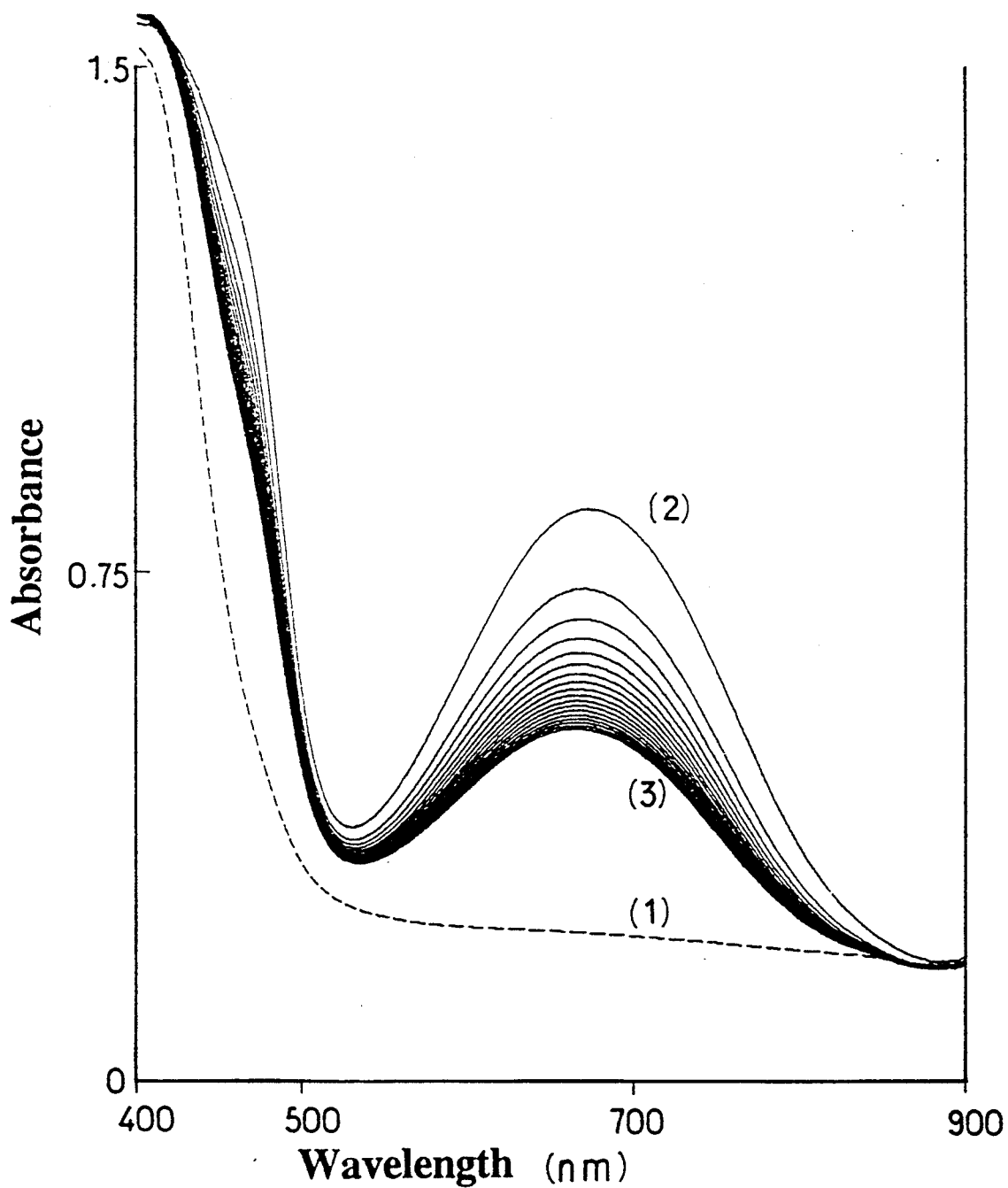
FIG. 1 shows visible light absorption spectra at 27° C. of the green film obtained in Example 1.

Visible light absorption spectra of the above-mentioned green film obtained in this example as measured at 27° C. are shown in FIG. 1.

The above film fixed in and maintaining said colored state was irradiated with visible light, whereupon it became uncolored and returned to its color before ultraviolet irradiation. Furthermore, the cycle comprising colored species fixation by means of ultraviolet light and color fading by means of visible light could be repeated with reproducibility.

EXAMPLE 2

Fully degassed styrene (16 g, 150 mmol) and 30 ml of dry toluene were added to 842 mg (1.80 mmol) of the 8'-methacryloxy-6'-nitro-1,3,3-trimethylspiro[indoline-2,2'(2'H)-1'-benzothiopyran] obtained in Reference Example 7. To this was added 114 mg (0.6 mmol) of α,α'-azobisisobutyronitrile as an initiator, and the polymerization reaction was carried out at 80° C. for 68 hours. The resultant reaction mixture was added dropwise to 500 ml of methanol, whereupon a light-yellow polymer precipitated out. The precipitate was separated using a glass filter and dried to give 9.82 g of a yellow powdery polymer.

Based on the physical characteristics mentioned below, this product was identified as a copolymer of the starting spiropyran compound and styrene. In its IR spectrum, absorptions due to a nitro group (1520 cm$^{-1}$, 1357 cm$^{-1}$) and an absorption due to a thiopyran ring (1645 cm$^{-1}$) were observed. GPC of this product gave a single peak, the number average molecular weight being Mn$=2.34 \times 10^4$ and the weight average molecular weight being Mw$=3.79 \times 10^4$. The elemental analysis data were: C 88.89%, H 7.63% and N 0.48%. Based on said data, the content of the spirothiopyran unit corresponding to general formula (I-1) was calculated to be 3.4 mole percent.

A 10-mg portion of this polymer was dissolved in 2 ml of benzene and the solution was cast onto a quartz plate, whereby a light-yellow film was obtained. This film was irradiated with ultraviolet rays about 350 nm in wavelength for 1 minute using an ultrahigh pressure mercury lamp and an ultraviolet band pass filter (Kenko U-350), whereupon it turned green, with an absorption maximum at λmax$=715$ nm. At room temperature, this green film did not become fully uncolored but was completely fixed at a colored species fixation percentage of 21%.

The above film fixed in and maintaining said colored state was irradiated with visible light, whereupon it become uncolored and returned to its color before ultraviolet irradiation. Furthermore, the cycle comprising colored species fixation by means of ultraviolet light and color fading by means of visible light could be repeated with reproducibility.

EXAMPLE 3

Fully degassed styrene (3.5 g, 34 mmol) and 15 ml of dry toluene were added to 452 mg (0.97 mmol) of 3,3-dimethyl-1-isopropyl-8'-methacryloxymethyl-6'-nitrospiro[indoline-2,2'(2'H)-1'-benzothiopyran] separately synthesized by following the general procedures of Reference Examples 1 to 7. To this was added 21 mg (0.13 mmol) of α,α-azobisisobutyronitrile as a reaction initiator, and the polymerization reaction was carried out at 80° C. for 70 hours. Thereafter, the reaction mixture was treated in the same manner as in Example 1 to give 967 mg of a yellow powdery polymer.

Based on the physical characteristics mentioned below, this product was identified as a copolymer of the starting spirothiopyran compound and styrene. In its IR spectrum, absorptions due to a nitro group (1522 and 1356 cm$^{-1}$) and an absorption due to a thiopyran ring (1646 cm$^{-1}$) were observed. GPC of this product gave a single peak, with a number average molecular weight of Mn$=1.38 \times 10^4$ and a weight average molecular weight of Mw$=2.15 \times 10^4$.

A 10-mg portion of this polymer was dissolved in 2 ml of benzene and the solution was cast onto a quartz plate, whereby a light-yellow film was obtained. This film was irradiated with ultraviolet rays about 350 nm in wavelength for 1 minute in the same manner as in Example 1, whereupon it turned green, with an absorption maximum wavelength of λmax$=691$ nm. At room temperature, this green film did not become completely uncolored but was fixed completely at a colored species fixation percentage of 46%.

The above film fixed in and maintaining said colored state was irradiated with visible light, whereupon it became uncolored and returned to its color before ultraviolet irradiation. Furthermore, the cycle comprising colored species fixation by means of ultraviolet light and color fading by means of visible light could be repeated with reproducibility.

Figure 2:
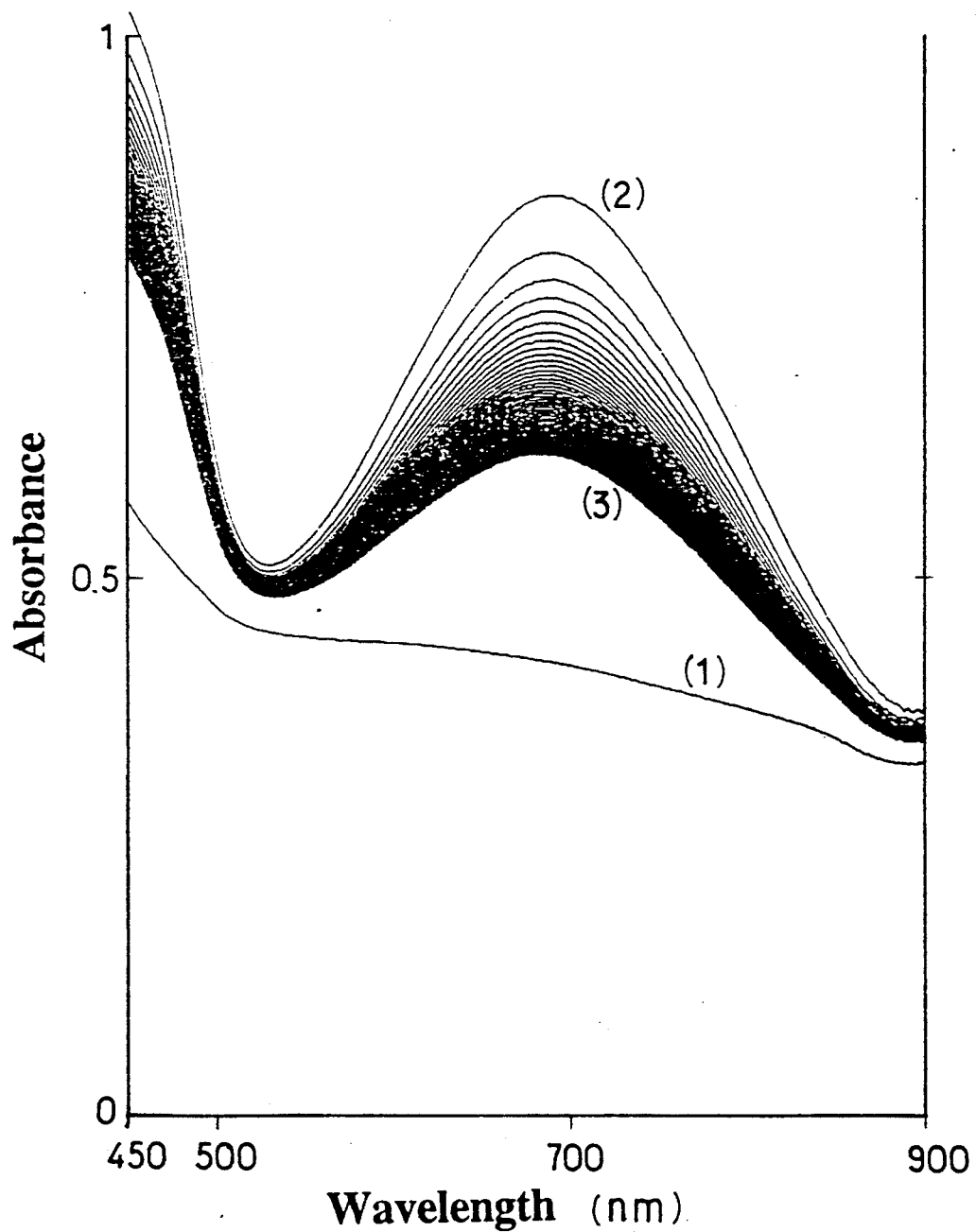
FIG. 2 shows visible light absorption spectra at 28.5° C. of the green film obtained in Example 3.

Visible light absorption spectra of the above green film as measured at 28.5° C. are shown in FIG. 2.

EXAMPLE 4

3,3-dimethyl-8'-methacryloxymethyl-6'-nitro-1-octadecylspiro[indoline-2,2'(2'H)-1'-benzothiopyran] (1.14 g, 1.70 mmol) separately synthesized following the general procedures of Reference Examples 1 to 7 was dissolved in 30 ml of toluene and 3.1 g (31.0 mmol) of methyl methacrylate. To this was added, under a nitrogen atmosphere and in the dark, 24 mg (0.13 mmol) of $\alpha,\alpha'$-azobisisobutyronitrile, and the polymerization reaction was carried out at 80° C. for 90 hours. Thereafter, the reaction mixture was treated in the same manner as in Example 1 to give 2.18 g of a yellow powdery polymer.

Based on the physical characteristics mentioned below, this product was identified as a copolymer of the starting spiropyran compound and methyl methacrylate.

In its IR spectrum, absorptions due to a nitro group (1518 and 1362 cm$^{-1}$) and to a thiopyran ring (1643 cm$^{-1}$) were observed. GPC of this product gave a single peak, with a number average molecular weight of $Mn = 3.58 \times 10^4$ and a weight average molecular weight of $Mw = 5.13 \times 10^4$. The elemental analysis data were: C 62.91%, H 8.17% and N 1.22%. Based on said data, the content of the spirothiopyran unit corresponding to general formula (I-1) was calculated to be 4.2 mole percent.

This polymer was formed into a light-yellow film by the same procedure as used in Example 1. After one-minute irradiation of the film with ultraviolet rays about 350 nm in wavelength, a green film was obtained. It had an absorption maximum wavelength $\lambda$max of 665 nm. At room temperature, this green film did not become completely uncolored but was fixed completely at a colored species fixation percentage of 81%.

The above film fixed in and maintaining said colored state was irradiated with visible light, whereupon it became uncolored and returned to its color before ultraviolet irradiation. Furthermore, the cycle comprising colored species fixation by means of ultraviolet light and color fading by means of visible light could be repeated with reproducibility.

Figure 3:
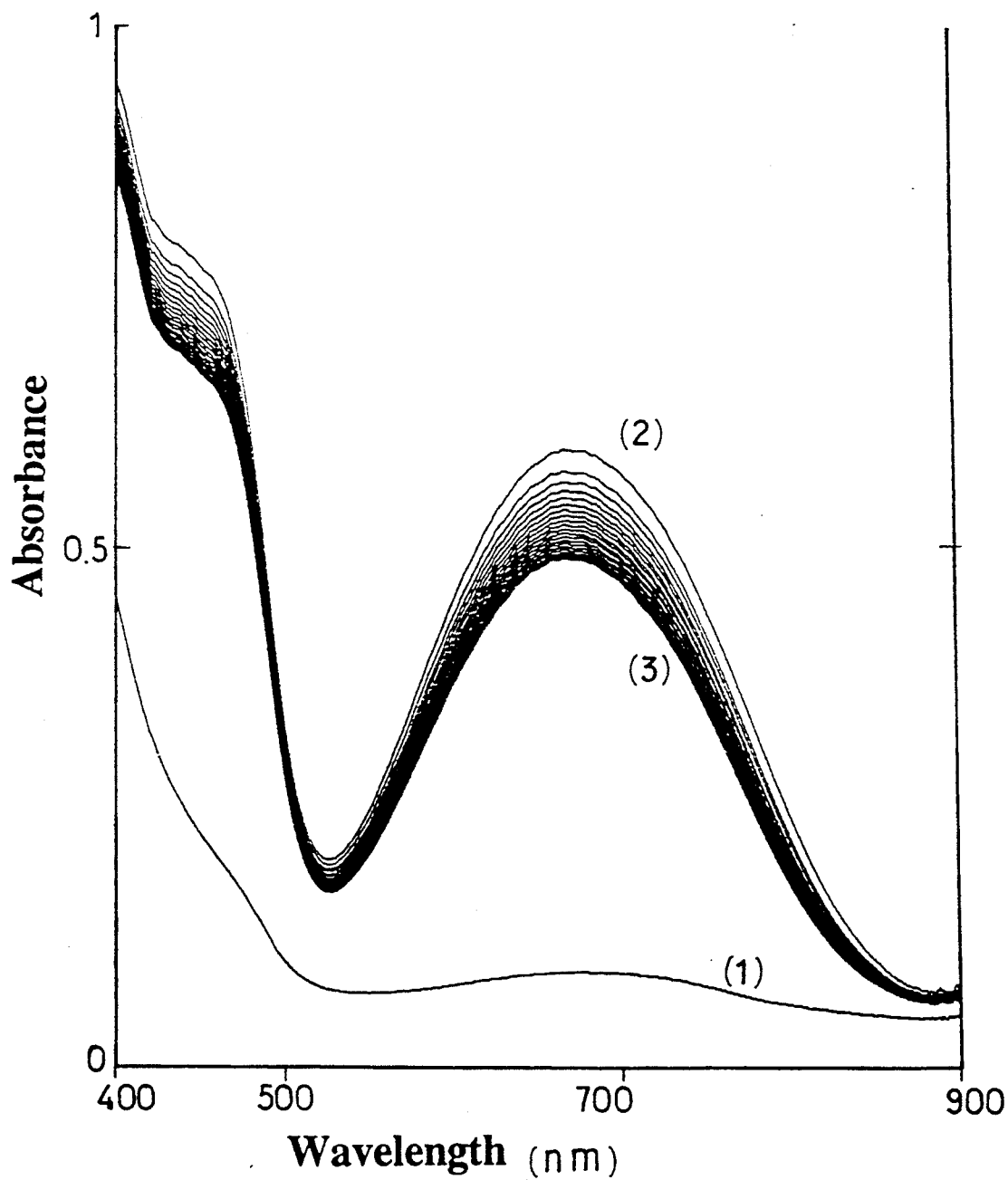
FIG. 3 shows visible light absorption spectra at 28° C. of the green film obtained in Example 4.

Visible light absorption spectra of the above green film as measured at 28° C. are shown in FIG. 3.

EXAMPLE 5

3,3-Dimethyl-8'-methacryloxymethyl-6'-nitro-1-octadecylspiro[indoline-2,2'(2'H)-1'-benzothiopyran] (572 mg, 0.85 mmol) was dissolved in 25 ml of toluene and 3.7 g (37 mmol) of methyl methacrylate. To this was added, under a nitrogen atmosphere and in the dark, 590 mg (3.2 mmol) of phenylmagnesium bromide, and the polymerization reaction was carried out at 70° C. for 19 hours. Thereafter, the reaction mixture was treated in the same manner as in Example 1 to give 2.24 g of a light-yellow powdery polymer.

Based on the physical characteristics mentioned below, this product was identified as a copolymer of the starting spiropyran compound and methyl methacrylate.

In its IR spectrum, absorptions due to a nitro group (1520 and 1355 cm$^{-1}$) and to a thiopyran ring (1645 cm$^{-1}$) were observed. In $^1$H-NMR (400 MHz), a single peak ascribable to an $\alpha$-methyl group of the methacrylic acid unit was found at $\delta = 1.56$ ppm, indicating that this polymer had almost 100% isotactic stereoregularity. GPC of this product gave the following results: number average molecular weight $Mn = 3.81 \times 10^4$ and weight average molecular weight $Mw = 2.07 \times 10^4$.

This polymer was formed into a light-yellow film by the same procedure as used in Example 1. The film was irradiated with ultraviolet rays about 350 nm in wavelength, whereupon it became a green film. Its absorption maximum wavelength $\lambda$max was 659 nm. At room temperature, this green film did not become fully uncolored but maintained a colored state. The colored species fixation percentage was 38%.

The above film fixed in and maintaining said colored state was irradiated with visible light, whereupon it became uncolored and returned to its color before ultraviolet irradiation. Furthermore, the cycle comprising colored species fixation by means of ultraviolet light and color fading by means of visible light could be repeated with reproducibility.

EXAMPLE 6

Dry toluene (50 ml) and 3.3 g (32.0 mmol) of fully degassed styrene were added to 1.22 mg (1.80 mmol) of 3,3-dimethyl-8'-methacryloxymethyl-6'-nitro-1-octadecylspiro[indoline-2,2'(2'H)-1'-benzothiopyran].

To this was added 45 mg (0.27 mmol) of $\alpha,\alpha'$-azobisisobutyronitrile as a reaction initiator, and the polymerization reaction was carried out at 80° C. for 70 hours. Thereafter, the reaction mixture was treated in the same manner as in Example 1 to give 1.64 g of a yellow powdery polymer.

Based on the physical characteristics mentioned below, this product was identified as a copolymer of the starting spiropyran compound and styrene. In its IR spectrum, absorptions due to a nitro group (1520 and 1361 cm$^{-1}$) and to a thiopyran ring (1645 cm$^{-1}$) were observed. GPC of this product gave a single peak, with a number average molecular weight of $Mn = 1.20 \times 10^4$ and a weight average molecular weight of $Mw = 1.89 \times 10^4$. The elemental analysis data were: C 56.95%, H 7.63% and N 1.15% and, based on these results, the content of the spiropyran unit of general formula (I-1) was calculated as 3.6 mole percent.

This polymer was formed into a light-yellow film by the same procedure as used in Example 1, and the film was irradiated with ultraviolet rays about 350 nm in wavelength for 1 minute, whereupon it turned to a green film. Its absorption maximum wavelength $\lambda$max was 693 nm. At room temperature, this green film did not become completely uncolored but maintained a colored state. The colored species fixation percentage was 31%.

The above film fixed in and maintaining said colored state was irradiated with visible light, whereupon it became uncolored and returned to its color before ultraviolet irradiation. Furthermore, the cycle comprising colored species fixation by means of ultraviolet light and color fading by means of visible light could be repeated with reproducibility.

Figure 4:
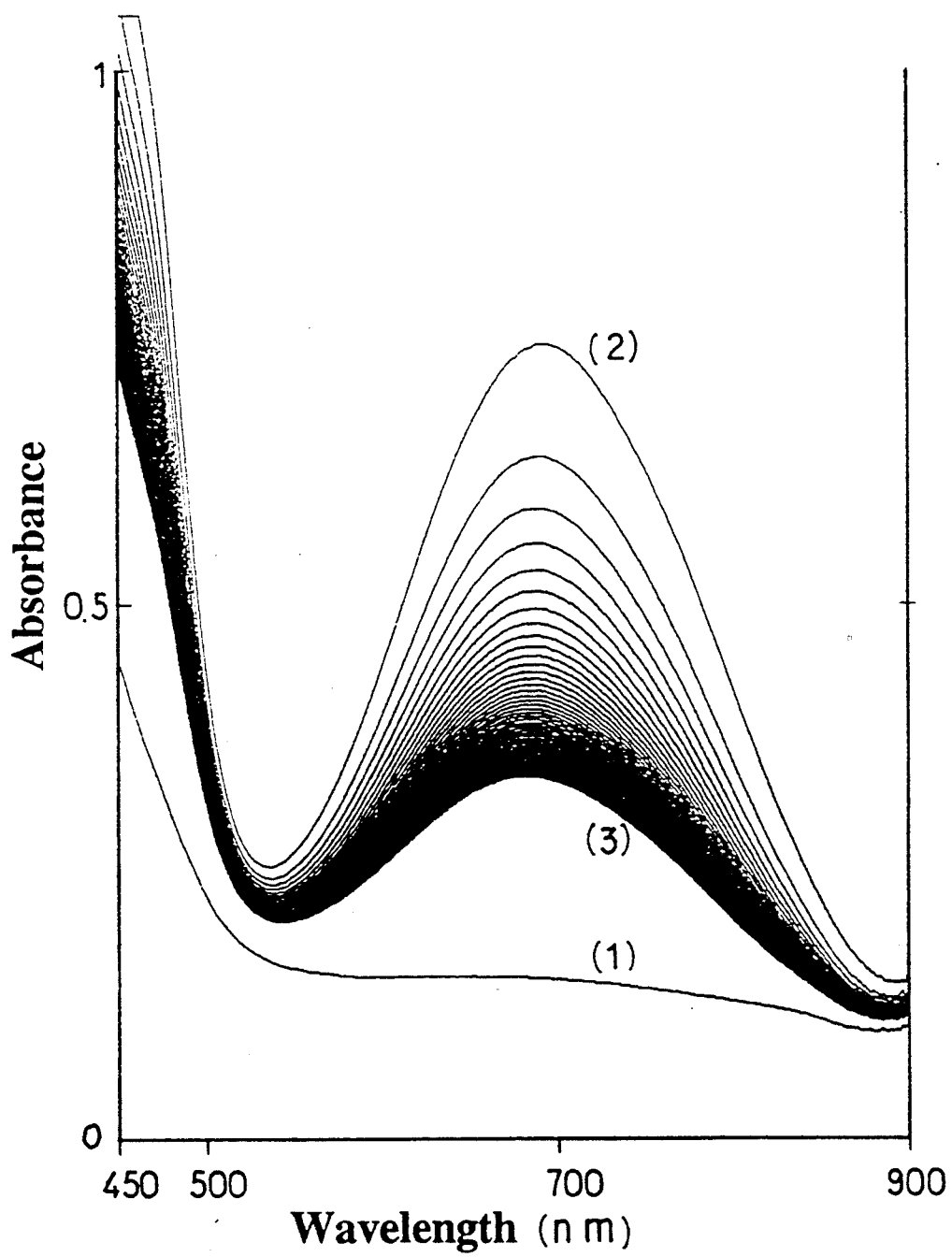
FIG. 4 shows visible light absorption spectra at 28° C. of the green film obtained in Example 6.

Visible light absorption spectra of the above green film as measured at 28° C. are shown in FIG. 4.

EXAMPLE 7

The 8-methacryloxymethyl-6-nitro-1',3',3'-trimethyl-spiro[2H-1-benzothiopyran-2,2'-indoline] (873 mg, 2.00 mmol) obtained in Reference Example 7 was dissolved in 20 ml of toluene. To this was added, in a nitrogen atmosphere and in the dark, 11.4 mg (0.60 mmol) of α,α'-azobisisobutyronitrile, and the polymerization reaction was carried out at 80° C. for 70 hours. The resultant yellow reaction mixture was added to 100 ml of methanol, whereupon a yellow precipitate formed. The precipitate was isolated by filtration and dried to give 0.15 g of a light-yellow polymer.

IR analysis of this product revealed a shift of the ester carbonyl absorption to 1733 cm$^{-1}$ and in addition, absorptions due to a nitro group (1521 and 1385 cm$^{-1}$) and to a thiopyran ring (1645 cm$^{-1}$). GPC gave a single peak, with a number average molecular weight of $Mn = 1.30 \times 10^3$ and a weight average molecular weight of $Mw = 1.90 \times 10^3$. The elemental analysis data were: C 65.89%, H 5.24% and N 6.62% and, based on these data, said product was identified as a homopolymer of the starting spiropyran compound.

This polymer was dissolved in dichloromethane and the solution was irradiated with ultraviolet rays in the same manner as in Example 1, whereupon its color changed to give a purplish solution. When irradiated with visible rays not shorter than 500 nm in wavelength, the color before ultraviolet irradiation was restored. Furthermore, the cycle comprising coloration by ultraviolet light and fading by visible light could be repeated with reproducibility. The absorption maximum wavelength λmax of this solution was 600 nm, indicating a shift by about 40 nm in the longer wavelength direction as compared with the starting monomer.

COMPARATIVE EXAMPLE 1

A composition obtained by blending polymethyl methacrylate with 10 mole percent of 8'-methacryloxymethyl-6'-nitro-1,3,3-trimethylspiro[indoline-2,2'-(2'H)-1'-benzothiopyran] obtained in Reference Example 7 was molded into a film in the same manner as in Example 1 and the film was subjected to ultraviolet irradiation in the same manner as in Example 1. The thus-obtained purple film immediately became uncolored at 23° C. and, after 6 hours, the colored species fixation percentage was 7%.

COMPARATIVE EXAMPLE 2

A composition obtained by blending polymethyl methacrylate with 9.5 mole percent of the same 3,3-dimethyl-8'-methacryloxymethyl-6'-nitro-1-octadecylspiro[indoline-2,2'(2'H)-1'-benzothiopyran] as used in Example 4 was molded into a film in the same manner as in Example 1 and the film was subjected to ultraviolet irradiation in the same manner as in Example 1. The thus-obtained violet film immediately lost its color at room temperature and, after overnight standing, the colored species fixation percentage was approximately 0%.

REFERENCE EXAMPLE 8

A mixture of 12.0 g of 5-nitrosalicylaldehyde and 100 ml of chloromethyl methyl ether was cooled on an ice bath, and 43.9 g of anhydrous aluminum chloride was added portionwise to said mixture, and the resultant mixture was stirred at room temperature for 10 minutes and then heated under reflux for 22 hours. Then, the reaction mixture was cooled on an ice bath and 200 ml of water was added thereto with vigorous stirring, whereupon white crystals precipitated out. These white crystals were taken out and dissolved in hot hexane, and the solution was filtered, and the mother liquor was cooled to give 14.9 g of 3-chloromethyl-5-nitrosalicylaldehyde as colorless needles (yield 72%).

$^1$H-NMR (CDCl$_3$); δ ppm 4.72 (s, 2H, —CH$_2$Cl), 8.56 (s, 2H, ArH), 10.00 (s, 1H, CHO), 12.10 (s, 1H, OH).

REFERENCE EXAMPLE 9

3-Chloromethyl-5-nitrosalicylaldehyde (10.5 g) was dissolved in 100 ml of toluene, and 11.4 g of silver methacrylate was added to the solution. This mixture was heated at 120° C. for 2.5 hours and then cooled to room temperature. The resultant precipitate was removed by filtration. The toluene solution obtained was concentrated under reduced pressure, whereby 12.7 g of 3-methacryloxymethyl-5-nitrosalicylaldehyde was obtained as a light-yellow powder (yield 98%).

$^1$H-NMR (CDCl$_3$); δ ppm 2.00 (t, 3H, CH$_3$), 5.34 (s, 2H, —CH$_2$—), 5.67 (t, 1H, vinyl), 6.22 (m, 1H, vinyl), 8.53 (m, 2H, ArH), 10.00 (s, 1H, CHO), 12.10 (brs, 1H, OH).

REFERENCE EXAMPLE 10

2-Methylbenzoselenazole (10.1 g) was dissolved in 100 ml of chloroform, then 10.0 g of methyl iodide was added to the solution, and the mixture was heated in an autoclave at 80° C. for 5 days. The crystals resulting from the reaction were taken out by filtration, washed with ether and dried to give 16.4 g of 2,3-dimethyl-benzoselenazolium iodide (yield 94%).

$^1$H-NMR (D$_2$O); δ ppm 3.13 (s, 3H, 2-methyl), 4.16 (s, 3H, 3-methyl), 7.73 (t, 1H, ArH), 7.83 (d, 1H, ArH), 8.13 (d, 1H, ArH), 8.15 (t, 1H, ArH).

REFERENCE EXAMPLE 11

3-Methacryloxymethyl-5-nitrosalicylaldehyde (10.6 g) and 13.6 g of 2,3-dimethylbenzoselenazolium iodide were added to 200 ml of methanol, and the mixture was heated under reflux and a solution of 34.2 g of piperidine in 50 ml of methanol was added dropwise to the refluxing mixture. Heating under reflux was continued for 27 hours, and the reaction mixture was then cooled to room temperature, and the resultant brown crystals were separated. 18.0 g of 8'-Methacryloxymethyl-3-methyl-6'-nitro-1-selenaspiro-[2H-1'-benzopyran-2,2'-benzoselenazoline] was thus obtained (Yield 100 %).

$^1$H-NMR (DMSO); δ ppm 1.91 (s, 3H, methacrylic-CH$_3$), 4.10 (s, 3H, N—CH$_3$), 5.03 (s, 2H, —CH$_2$—), 5.70 (s, 1H, vinyl), 6.06 (s, 1H, vinyl), 7.58 (t, 1H, 6-H), 7.71 (t, 1H, 5-H), 7.90 (d, 1H, 3'-H), 8.05 (d, 1H, 4-H), 8.17 (d, 1H, 7'-H), 8.32 (d, 1H, 7-H), 8.53 (d, 1H, 4'-H), 8.70 (d, 1H, 5'-H).

REFERENCE EXAMPLE 12

Octadecyl parachlorobenzenesulfonate (19.1 g) was added to 6.17 g of 2-methylbenzoselenazole, and the mixture was heated at 130° C. for 6 hours. The crystals yielded by the reaction were washed with ether and then recrystallized from n-propanol. Drying of the crystals gave 12.8 g of 2-methyl-3-octadecylbenzoselenazolium parachlorobenzenesulfonate (yield 65%).

$^1$H-NMR (CDCl$_3$); δ ppm 0.88 (t, 3H, methyl), 1.25 (m, 30H, —(CH$_2$)—$_{15}$), 1.84 (qui, 2H, —CH$_2$—C—N), 3.27 (s, 3H, 2-methyl), 4.68 (t, 2H, —CH$_2$—N), 7.2–8.3 (m, 8H, ArH).

REFERENCE EXAMPLE 13

3-Methacryloxymethyl-5-nitrosalicylaldehyde (2.07 g) and 5.00 g of 2-methyl-3-octadecylbenzoselenazolium parachlorobenzenesulfonate were added to 80 ml of methanol, and a solution of 0.81 g of piperidine in 20 ml of methanol was added dropwise in portions to the mixture at room temperature. After heating under reflux for 5 hours, the reaction mixture was cooled. The resultant purple solid was collected by filtration and separated and purified by silica gel column chromatography to give 4.67 g of 8'-methacryloxymethyl-6'- nitro-3-octadecyl-1-selenaspiro[2H-1'-benzopyran-2,2'-benzoselenazoline] (yield 86%).

$^1$H-NMR (CDCl$_3$); δ ppm 0.88 (t, 3H, methyl), 1.23 (m, 30H, —(CH$_2$)—$_{15}$), 1.92 (qui, 2H, —CH$_2$—C—N), 2.03 (s, 3H, methacrylic-CH$_3$), 4.46 (t, 2H, —CH$_2$—N), 5.23 (s, 2H, —CH$_2$—Ar), 5.63 (s, 1H, vinyl), 6.24 (s, 1H, vinyl), 7.66 (br. d, 1H, 4'-H), 8.81 (br. s, 1H, 3'-H), 7.2–8.1 (m, 6H, ArH).

REFERENCE EXAMPLE 14

Octadecyl parachlorobenzenesulfonate (11.5 g) was added to 3.96 g of 2,5-dimethylbenzoselenazole, and the mixture was heated at 130° C. for 6 hours. The crystals yielded by the reaction were washed with ether and then recrystallized from ethyl acetate. Drying of the crystals gave 7.42 g of 2,5-dimethyl-3-octadecylbenzoselenazolium parachlorobenzenesulfonate (yield 61%).

$^1$H-NMR (CDCl$_3$); δ ppm 0.88 (t, 3H, methyl), 1.25 (m, 30H, —(CH$_2$)—$_{15}$), 1.86 (qui, 2H, —CH$_2$—C—N), 2.58 (s, 3H, 5-methyl), 3.29 (s, 3H, 2-methyl), 4.67 (t, 2H, —CH$_2$—N), 7.2–8.1 (m, 7H, ArH).

REFERENCE EXAMPLE 15

3-Methacryloxymethyl-5-nitrosalicylaldehyde (2.83 g) and 7.00 g of 2,5-dimethyl-3-octadecylbenzoselenazolium parachlorobenzenesulfonate were added to 80 ml of methanol, and a solution of 1.11 g of piperidine in 20 ml of methanol was added dropwise in portions to the mixture at room temperature. After heating under reflux, the reaction mixture was cooled. The resultant purple solid was collected by filtration and isolated and purified by silica gel column chromatography to give 6.65 g of 8'-methacryloxymethyl-5-methyl-6'-nitro-3-octadecyl-1-selenaspiro-[2H-1'-benzopyran-2,2'-benzoselenazoline] (yield 88%).

$^1$H-NMR (CDCl$_3$); δ ppm 0.88 (t, 3H, methyl), 1.25 (m, 30H, —(CH$_2$)—$_{15}$), 1.90 (qui, 2H, —CH$_2$—C—N), 2.05 (s, 3H, methacrylic-CH$_3$), 2.50 (s, 3H, CH$_3$—Ar), 4.44 (t, 2H, —CH$_2$—N), 5.24 (s, 2H, —CH$_2$—Ar), 5.65 (s, 1H, vinyl), 6.27 (s, 1H, vinyl), 7.53 (br. d, 1H, 4'-H), 8.80 (br. s, 1H, 3'-H), 7.3–7.9 (m, 5H, ArH).

REFERENCE EXAMPLE 16

Octadecyl parachlorobenzenesulfonate (11.1 g) was added to 5.13 g of 5-methoxy-2-methylbenzoselenazole, and the mixture was heated at 130° C. for 5 hours. The crystals yielded by the reaction were washed with ether and then recrystallized from benzene to give 9.98 g of 5-methoxy-2-methyl-3-octadecylbenzoselenazolium parachlorobenzenesulfonate (yield 67%).

$^1$H-NMR (CDCl$_3$); δ ppm 0.88 (t, 3H, methyl), 1.25 (m, 30H, —(CH$_2$)—$_{15}$), 1.84 (qui, 2H, —CH$_2$—C—N), 3.22 (s, 3H, 2-methyl), 3.94 (s, 3H, CH$_3$O), 4.64 (t, 2H, —CH$_2$—N), 7.1–8.1 (m, 7H, ArH).

REFERENCE EXAMPLE 17

3-Methacryloxymethyl-5-nitrosalicylaldehyde (2.20 g) and 5.57 g of 5-methoxy-2-methyl-3-octadecylbenzoselenazolium chlorobenzenesulfonate were added to 80 ml of methanol, and a solution of 0.90 g of piperidine in 20 ml of methanol was added dropwise to the mixture at room temperature. After heating under reflux for 5 hours, the reaction mixture was cooled. The resultant purple solid was collected by filtration and subjected to silica gel column chromatography for separation and purification to give 4.35 g of 8'-methacryloxymethyl-5-methoxy-6'-nitro-3-octadecyl-1-selenaspiro[2H-1'-benzopyran-2,2'-benzoselenazoline] (yield 72%).

$^1$H-NMR (CDCl$_3$); δ ppm 0.88 (t, 3H, methyl), 1.25 (m, 30H, —(CH$_2$)—$_{15}$), 1.92 (qui, 2H, —CH$_2$—C—N), 2.03 (s, 3H, methacrylic-CH$_3$), 3.91 (s, 3H, CH$_3$O), 4.40 (t, 2H, —CH$_2$—N), 5.23 (s, 2H, —CH$_2$—), 5.62 (s, 1H, vinyl), 6.24 (s, 1H, vinyl), 7.59 (br. d, 1H, 4'-H), 8.79 (br. s, 1H, 3'-H), 7.0–8.0 (m, 5H, ArH).

REFERENCE EXAMPLE 18

Octadecyl parachlorobenzenesulfonate (11.2 g) was added to 5.84 g of 5,6-dimethoxy-2-methylbenzoselenazole, and the mixture was heated at 130° C. for 6 hours. The crystals yielded by the reaction were washed with ether and then recrystallized from a solvent mixture composed of hexane and benzene. The subsequent drying gave 10.4 g of 5,6-dimethoxy-2-methyl-3-octadecylbenzoselenazolium parachlorobenzenesulfonate (yield 65%).

$^1$H-NMR (CDCl$_3$); δ ppm 0.88 (t, 3H, methyl), 1.25 (m, 30H, —(CH$_2$)—$_{15}$), 1.83 (qui, 2H, —CH$_2$—C—N), 3.09 (s, 3H, 2-methyl), 3.98 (s, 3H, 5—CH$_3$O or 6—CH$_3$O), 4.03 (s, 3H, 6—CH$_3$O or 5—CH$_3$O), 4.63 (t, 2H, —CH$_2$—N), 7.2–7.9 (m, 6H, ArH).

REFERENCE EXAMPLE 19

3-Methacryloxymethyl-5-nitrosalicylaldehyde (2.36 g) and 6.24 g of 5,6-dimethoxy-2-methyl-3-octadecylbenzoselenazolium parachlorobenzenesulfonate were added to 80 ml of methanol, and a solution of 0.94 g of piperidine in 20 ml of methanol was added dropwise to the mixture at room temperature. After heating under reflux for 5 hours, the reaction mixture was cooled. The resultant purple solid was collected by filtration and subjected to silica gel column chromatography for separation and purification to give 5.17 g of 8'-methacryloxymethyl-5,6-dimethoxy-6'-nitro-3-octadecyl-1-selenaspiro-[2H-1'-benzopyran-2,2'-benzoselenazoline] (yield 77%).

$^1$H-NMR (CDCl$_3$); δ ppm 0.87 (t, 3H, methyl), 1.24 (m, 30H, —(CH$_2$)—$_{15}$), 1.92 (qui, 1H, —CH$_2$—C—N), 2.03 (s, 3H, methacrylic-CH$_3$), 3.99 (s, 3H, 5-CH$_3$O or 6-CH$_3$O), 4.00 (s, 3H, 6-CH$_3$O or 5-CH$_3$O), 4.41 (t, 2H, —CH$_2$—N), 5.19 (s, 2H, —CH$_2$—Ar), 5.62 (s, 1H, vinyl), 6.23 (s, 1H, vinyl), 7.52 (br. d, 1H, 4'-H), 8.77 (br. s, 1H, 3'-H), 6.9–8.0 (m, 4H, ArH).

EXAMPLE 8

The 8'-methacryloxymethyl-3-methyl-6'-nitro-1-selenaspiro-[2H-1'-benzopyran-2,2'-benzoselenazoline] (290 mg, 0.64 mmol) obtained in Reference Example 11 was dissolved in 30 ml of N,N-dimethylformamide distilled under a nitrogen stream, and 3.7 g (37.0 mmol) of dried methyl methacrylate was added to the solution. To this was added 53 mg (0.32 mmol) of α,α'-azobisisobutyronitrile as a polymerization initiator, and the polymerization reaction was carried out at 80° C. for 45 hours. Methanol (500 ml) was added dropwise to the solution after reaction, whereupon a purple solid precipitated out. The precipitate was separated by using a glass filter and dried to give 2.80 g of a polymer.

Based on the physical characteristics mentioned below, this product was identified as a copolymer of the starting spiropyran compound and methyl methacrylate. In its IR spectrum, strong absorptions due to an ester carbonyl group (1720 to 1745 cm$^{-1}$) and to a nitro group (1545 and 1375 cm$^{-1}$) were observed. GPC (solvent=tetrahydrofuran, temperature=40° C., based on the standard polystyrene) of this product gave a single peak, with a number average molecular weight of $Mn=1.86\times10^4$ and a weight average molecular weight of $Mw=2.31\times10^4$. The elemental analysis data were: C 58.62%, H 7.93% and N 1.04% and, based on these data, the content of the spiropyran unit of general formula (I-2) in said polymer was identified as 3.0 mole percent.

A 10-mg portion of this polymer was dissolved in 2 ml of benzene and the solution was cast onto a quartz plate to give a purple film. This film initially had an absorption maximum at 568 nm but, when it was irradiated with visible light using a 500-W ultrahigh pressure mercury lamp equipped with a cut-off filter allowing passage of visible rays not shorter than 500 nm in wavelength, the previous absorption maximum disappeared and the film became colorless and transparent. This colorless film gradually turned to a purple color at room temperature (22° C.). The thermal half-life ($\tau_{\frac{1}{2}}$) of the uncolored species as calculated from the first-order rate constant for the thermal coloration of the uncolored species was 3.8 hours. Thus life prolongation as much as 29 times the thermal half-life of the starting monomer (chloroform solution) was achieved. This film did not become fully colored at room temperature but was stably fixed in and maintained a semi-uncolored state at an uncolored species fixation percentage of 31%. Visible light absorption spectra indicating this fact are shown in FIG. 5.

Thus, upon ultraviolet irradiation, this film turned into the colored species, which, upon visible light irradiation, again shifted to the colorless state (uncolored species) and, when allowed to stand at 22° C., maintained the semi-uncolored state at an uncolored species fixation percentage of 31%. This cycle could be repeated.

The "uncolored species fixation percentage" as so termed herein is defined as follows (the same shall apply in the subsequent examples):

Uncolored species fixation percentage (%) =

$$\frac{\begin{pmatrix}\text{Maximum}\\\text{absorbance}\end{pmatrix} - \begin{pmatrix}\text{Absorbance in}\\\text{fixed state}\end{pmatrix}}{\begin{pmatrix}\text{Maximum}\\\text{absorbance}\end{pmatrix} - \begin{pmatrix}\text{Absorbance in}\\\text{uncolored state}\end{pmatrix}} \times 100$$

In the above expression, the "absorbance in fixed state" means the absorbance at the absorption maximum wavelength in a state such that the increase in absorbance is substantially unobservable any more generally after the lapse of about 24 hours following visible light irradiation, although this period may vary depending on the sample to be tested. The "absorbance in uncolored state" means the absorbance at the above-mentioned absorption maximum wavelength immediately after visible light irradiation for fading.

EXAMPLE 9

8'-Methacryloxymethyl-5-methoxy-3-methyl-6'-nitro-1-selenaspiro-[2H-1'-benzopyran-2,2'-benzoselenazoline] (440 mg, 0.90 mmol) separately synthesized following the general procedures of Reference Examples 8 to 11 was dissolved in 40 ml of N,N-dimethylformamide distilled under a nitrogen stream, and 7.0 g (70.0 mmol) of dried methyl methacrylate was added to the solution. Thereto was added 48 mg (0.29 mmol) of α,α'-azobisisobutyronitrile as a polymerization initiator, and the polymerization reaction was carried out at 80° C. for 12 hours. Thereafter, the reaction mixture was treated in the same manner as in Example 8 to give 6.45 g of a purple powdery polymer.

Based on the physical characteristics mentioned below, this product was identified as a copolymer of the starting spiropyran compound and methyl methacrylate. In its IR spectrum, strong absorptions due to an ester carbonyl group (1730 to 1745 cm$^{-1}$) and to a nitro group (1540 and 1355 cm$^{-1}$) were observed. GPC (solvent=tetrahydrofuran, temperature=40° C., based on the standard polystyrene) of this product gave a single peak, with a number average molecular weight of $Mn=2.17\times10^4$ and a weight average molecular weight of $Mw=3.45\times10^4$. The content of the spiropyran unit of general formula (I-2) in this polymer was calculated to be 1.1 mole percent from the comparison between the absorptivity coefficient ($\epsilon=33000$) of a chloroform solution of the starting spiropyran monomer at λmax and that ($\epsilon=1700$) of the product polymer.

This polymer was molded into a purple film by the same procedure as used in Example 8. When the film was irradiated with visible rays not shorter than 500 nm in wavelength, the initially observed absorption maximum peak at 534 nm disappeared and the film became colorless and transparent. This film gradually became colored at room temperature. The thermal half-life ($\tau_{\frac{1}{2}}$) at 21° C. was 6.4 hours, which was as much as 58 times longer than the thermal half-life of the starting monomer (chloroform solution).

Thus, upon ultraviolet irradiation, the above film maintaining its semi-uncolored state became colored and returned to its original color. When irradiated again with visible light, said film shifted to the colorless state (uncolored system) and, when allowed to stand at a temperature around room temperature, it maintained the semi-uncolored state. This cycle could be repeated.

EXAMPLE 10

8'-Methacryloxy-3,5-dimethyl-6'-nitro-1-selenaspiro[2H-1'-benzopyran-2,2'-benzoselenazoline] (320 mg, 0.68 mmol) separately synthesized following the general procedures of Reference Examples 8 to 11 was dissolved in 40 ml of N,N-dimethylformamide distilled under a nitrogen stream, and 9.5 g (95.0 mmol) of dried methyl methacrylate was added to the solution. To this mixture was added 41 mg (0.25 mmol) of α,α'-azobisisobutyronitrile as a polymerization initiator, and the polymerization reaction was carried out at 80° C. for 11 hours. The reaction mixture was treated in the same manner as in Example 8 to give 7.23 g of a purple powdery polymer.

Based on the physical characteristics mentioned below, this product was identified as a copolymer of the starting spiropyran compound and methyl methacrylate. In its IR spectrum, strong absorptions due to an ester carbonyl group (1732 to 1740 cm$^{-1}$) and to a nitro group (1528 and 1383 cm$^{-1}$) were observed. GPC (solvent = tetrahydrofuran, temperature = 40° C, in polystyrene equivalent) of this product gave a single peak, with a number average molecular weight of Mn = 2.72 × 10$^4$ and a weight average molecular weight of Mw = 4.00 × 10$^4$. The elemental analysis data were: C 58.14%, H 8.01% and N 0.78% and, based on these data, the content of the spiropyran unit of general formula (I-2) in this polymer was found to be 2.0 mole percent.

This polymer was molded into a purple film by the same procedure as used in Example 8. When the film was irradiated with visible light not shorter than 500 nm in wavelength, the initially observed maximum absorption peak at 544 nm disappeared and the film became colorless and transparent. This film became gradually colored at room temperature and showed a thermal half-life ($\tau_{\frac{1}{2}}$) of 6.1 hours as measured at 21° C., which was 46 times longer than the thermal half-life of the starting monomer (chloroform solution).

Thus, upon ultraviolet irradiation, the above film maintaining the semi-uncolored state became colored and returned to its original color and again shifted to the colorless state (uncolored system) upon visible light irradiation. When subsequently allowed to stand at a temperature around room temperature, the film maintained the semi-uncolored state. This cycle could be repeated.

EXAMPLE 11

8'-Methacryloxymethyl-5-methoxy-3-methyl-6'-nitro-1-selenaspiro[2H-1'-benzopyran-2,2'-benzoselenazoline] (318 mg, 0.65 mmol) was dissolved in 30 ml of N,N-dimethylformamide distilled under a nitrogen stream, and 8.05 g (77.4 mmol) of thoroughly degassed styrene was added to the solution. To this was added 156 mg (0.95 mmol) of $\alpha,\alpha'$-azobisisobutyronitrile as a polymerization initiator, and the polymerization reaction was carried out at 90° C. for 42 hours. The reaction mixture was treated in the same manner as in Example 8 to give 2.36 g of a purple powdery polymer.

Based on the physical characteristics mentioned below, this product was identified as a copolymer of the starting spiropyran compound and styrene. GPC (solvent = tetrahydrofuran, temperature = 40° C., in polystyrene equivalent) gave a single peak, with a number average molecular weight of Mn = 5.29 × 10$^3$ and a weight average molecular weight of Mw = 7.43 × 10$^3$. In its IR spectrum strong absorptions due to an ester carbonyl group (1735 to 1748 cm$^{-1}$) and to a nitro group (1520 and 1365 cm$^{-1}$) were observed. The elemental analysis data were: C 87.47%, H 7.37% and N 1.06% and, based on these data, the content of the spiropyran unit of general formula (I-2) in this polymer was found to be 3.6 mole percent.

A 10-mg portion of this polymer was dissolved in 2 ml of chloroform. The solution was irradiated with visible rays not shorter than 500 nm in wavelength, whereupon the initially observed maximum absorption peak at 583 nm disappeared and the solution became colorless. This solution gradually turned into a purple color at room temperature. Its thermal half-life ($\tau_{\frac{1}{2}}$) was 26.4 minutes, which was 4.0 times longer than the thermal half-life of the starting monomer (chloroform solution).

A film obtained by casting this polymer solution onto a quartz plate was irradiated with visible light in the same manner as in Example 8, whereupon it became colorless and transparent. At room temperature, this film did not become fully colored but was completely fixed in and maintained a semi-uncolored state at an uncolored species fixation percentage of 35%. Visible light absorption spectra indicating this fact are shown in FIG. 6.

Thus, upon ultraviolet irradiation, the above film maintaining said semi-uncolored state became colored and returned to its original color and again shifted to the colorless state (uncolored system) upon visible light irradiation. When subsequently allowed to stand at a temperature around room temperature, it maintained the semi-uncolored state. This cycle could be repeated.

EXAMPLE 12

The same 8'-methacryloxymethyl-5-methoxy-3-methyl-6'-nitro-1-selenaspiro-[2H-1'-benzopyran-2,2'-benzoselenazoline] (477 mg, 0.98 mmol) as used in Example 2 was dissolved in 20 ml of N,N-dimethylformamide distilled under a nitrogen stream. To the solution was added 113 mg (0.69 mmol) of $\alpha,\alpha'$-azobisisobutyronitrile as a polymerization initiator, and the polymerization reaction was carried out at 80° C. for 24 hours. Methanol (100 ml) was added to the solution obtained after reaction, whereupon a purple precipitate formed. This was isolated by centrifugation and dried to give 210 mg of a polymer.

IR analysis revealed that this product showed shifting of the absorption due to ester carbonyl group to 1735 cm$^{-1}$ and, in addition, showed absorptions due to a nitro group (1532 and 1385 cm$^{-1}$). GPC gave a single peak, with a number average molecular weight of $\overline{Mn}$ = 1.85 × 10$^3$ and a weight average molecular weight of $\overline{Mw}$ = 2.21 × 10$^3$. The elemental analysis data were: C 53.87%, H 4.04% and N 5.98% and, based on these results, said product was identified as a homopolymer of the starting spiropyran compound.

A chloroform solution of this polymer had a purple color at room temperature (20° C.), with λmax = 575 nm. This purple solution was irradiated with visible light in the same manner as in Example 8, whereupon the previously-mentioned maximum absorption peak disappeared and the solution became colorless. This colorless solution became gradually colored at room temperature.

EXAMPLE 13

8'-Methacryloxymethyl-6'-nitro-3-octadecyl-1-selenaspiro-[2H-1'-benzopyran-2,2'-benzoselenazoline] (198 mg, 0.285 mmol) was dissolved in 30 ml of N,N-dimethylformamide distilled under a nitrogen stream. To this was added 5.90 g (59.0 mmol) of dried methyl methacrylate. To this was added 47 mg (0.29 mmol) of $\alpha,\alpha'$-azobisisobutyronitrile as a polymerization initiator, and the polymerization reaction was carried out at 60° C. for 24 hours. Methanol (500 ml) was added dropwise to the solution after reaction, whereupon a purple solid precipitated out. The precipitate was separated using a glass filter and dried to give 3.20 g of a polymer.

Based on the physical characteristics mentioned below, this product was identified as a copolymer of the starting spiropyran compound and methyl methacrylate. In its IR spectrum, strong absorptions due to an ester carbonyl group (1720 to 1745 cm$^{-1}$) and to a nitro group (1545 and 1375 cm$^{-1}$) and an absorption due to an alkyl group (2920 cm$^{-1}$) were observed. GPC (solvent = tetrahydrofuran, temperature = 40° C., in polystyrene equivalent) of this product gave a single peak, with a number average molecular weight of $\overline{M}n = 3.7 \times 10^4$ and a weight average molecular weight of $\overline{M}w = 9.4 \times 10^4$. The elemental analysis data were: C 59.04%, H 8.02% and N 0.30% and, based on these data, the content of the spiropyran unit of general formula (I-2) in this polymer was identified as 1.1 mole percent.

A 10-mg portion of this polymer was dissolved in 2 ml of benzene and the solution was cast onto a quartz plate to give a purple film. This film initially had an absorption maximum at 562 nm but, when irradiated with visible light using a 500-W ultrahigh pressure mercury lamp equipped with a cut-off filter allowing passage of visible rays not shorter than 500 nm in wavelength, the previous maximum absorption peak disappeared and the film became colorless and transparent. This colorless film became gradually colored at room temperature (25° C.) but did not become completely colored and was stably fixed in and maintained a semi-uncolored state at an uncolored species fixation percentage of 61%. Visible light absorption spectra indicating this fact are shown in FIG. 7.

Thus, upon ultraviolet irradiation, this film turned into the colored species and, upon visible light irradiation, it again shifted to the colorless state (uncolored species). When subsequently allowed to stand at 25° C., it maintained the semi-uncolored state at an uncolored species fixation percentage of 61%. This cycle could be repeated.

EXAMPLE 14

8'-Methacryloxymethyl-5-methyl-6'-nitro-3-octadecyl-1-selenaspiro-[2H-1'-benzopyran-2,2'-benzoselenazoline] (200 mg, 0.282 mmol) was dissolved in 30 ml of N,N-dimethylformamide distilled under a nitrogen stream. To this was added 5.80 g (58.0 mmol) of dried methyl methacrylate. Thereto was added 46 mg (0.28 mmol) of $\alpha,\alpha'$-azobisisobutyronitrile as a polymerization initiator, and the polymerization reaction was carried out at 60° C. for 24 hours. Methanol (500 ml) was added dropwise to the solution after reaction, whereupon a purple precipitate formed. The precipitate was separated using a glass filter and dried to give 3.36 g of a polymer.

Based on the physical characteristics mentioned below, this product was identified as a copolymer of the starting spiropyran compound and methyl methacrylate. In its IR spectrum, strong absorptions due to an ester carbonyl group (1720 to 1745 cm$^{-1}$) and to a nitro group (1545 and 1375 cm$^{-1}$) as well as an absorption due to an alkyl group (2920 cm$^{-1}$) were observed. GPC (solvent=tetrahydrofuran, temperature=40° C., in polystyrene equivalent) of this product gave a single peak, with a number average molecular weight of $\overline{M}n = 4.4 \times 10^4$ and a weight average molecular weight of $\overline{M}w = 11.9 \times 10^4$. The elemental analysis data were: C 59.04%, H 7.95% and N 0.30% and, based on these data, the content of the spiropyran unit of general formula (I-2) in this polymer was identified as 1.1 mole percent.

A 10-mg portion of this polymer was dissolved in 2 ml of benzene, and the solution was cast onto a quartz plate, whereby a purple film was obtained. This film initially had an absorption maximum at 561 nm but, after visible light irradiation using a 500-W ultrahigh pressure mercury lamp equipped with a cut-off filter allowing passage of visible rays not shorter than 500 nm, the previous maximum absorption peak disappeared and the film became colorless and transparent. At room temperature (25° C.), this colorless film became gradually colored but did not become fully colored. It was fixed in and maintained a semi-uncolored state at an uncolored species fixation percentage of 61%.

Thus, this film turned into the colored species upon ultraviolet irradiation and again shifted to the colorless state (uncolored species) again upon visible light irradiation. When subsequently allowed to stand at 25° C., it maintained the semi-uncolored state at an uncolored species fixation percentage of 61%. This cycle could be repeated.

EXAMPLE 15

8'-Methacryloxymethyl-5-methoxy-6'-nitro-3-octadecyl-1-selenaspiro[2H-1'-benzopyran-2,2'-benzoselenazoline] (206 mg, 0.284 mmol) was dissolved in 30 ml of N,N-dimethylformamide distilled-under a nitrogen stream. To this was added 6.00 g (60.0 mmol) of dried methyl methacrylate. Thereto was added 47 mg (0.29 mmol) of $\alpha,\alpha'$-azobisisobutyronitrile as a polymerization initiator, and the polymerization reaction was carried out at 60° C. for 24 hours. Methanol (500 ml) was added dropwise to the solution after reaction, whereupon a purple solid precipitated out. The precipitate was separated using a glass filter and dried to give 2.68 g of a polymer.

Based on the physical characteristics mentioned below, this product was identified as a copolymer of the starting spiropyran compound and methyl methacrylate. In its IR spectrum, there were observed strong absorptions due to an ester carbonyl group (1720 to 1745 cm$^{-1}$), a nitro group (1542 and 1372 cm$^{-1}$) and an alkyl group (2930 cm$^{-1}$). GPC (solvent=tetrahydrofuran, temperature=40° C., in polystyrene equivalent) of this product gave a single peak, with $\overline{M}n = 4.0 \times 10^4$ and $\overline{M}w = 8.6 \times 10^4$. The elemental analysis data were: C 58.78%, H 7.78% and N 0.27% and, based on these data, the content of the spiropyran unit of general formula (I-2) in this polymer was identified as 1.0 mole percent.

A 10-mg portion of this polymer was dissolved in 2 ml of benzene and the solution was cast onto a quartz plate to give a purple film. This film initially had an absorption maximum at 561 nm but, after visible light irradiation using a 500-W ultrahigh pressure mercury lamp equipped with a cut-off filter allowing passage of visible rays of 500 nm and longer, the previous maximum absorption peak disappeared and the film became colorless and transparent. At room temperature, this colorless film gradually turned into a purple color. The thermal half-life ($\tau_{\frac{1}{2}}$) of the uncolored species as calculated from the first order rate constant for the thermal coloration of the uncolored species was 79.4 days and thus the life was prolonged as much as 45,700 times as compared with the thermal half-life of the starting monomer (chloroform solution). At room temperature, this film did not become fully colored but was fixed in and maintained a semi-uncolored state at an uncolored species fixation percentage of 85%.

Thus, upon ultraviolet irradiation, this film turned into the colored species and, upon visible light irradiation, again shifted to the colorless state (uncolored species). When subsequently allowed to stand at 25° C., it maintained the semi-uncolored state at an uncolored species fixation percentage of 85%. This cycle could be repeated.

EXAMPLE 16

8'-Methacryloxymethyl-5,6-dimethoxy-6'-nitro-3octadecyl-1-selenaspiro-[2H-1'-benzopyran-2,2'-benzoselenazoline] (217 mg, 0.287 mmol) was dissolved in N,N-dimethylformamide distilled under a nitrogen stream. To this was added 6.00 g (60.0 mmol) of dried methyl methacrylate. Thereto was added 48 mg (0.29 mmol) of α,α'-azobisisobutyronitrile as a polymerization initiator, and the polymerization reaction was carried out at 60° C. for 24 hours. Methanol (500 ml) was added dropwise to the solution after reaction, whereupon a purple solid precipitated out. The precipitate was separated using a glass filter and dried to give 3.13 g of a polymer.

Based on the physical characteristics mentioned below, this product was identified as a copolymer of the starting spiropyran compound and methyl methacrylate. In its IR spectrum, strong absorptions due to an ester carbonyl group (1730 to 1745 cm$^{-1}$) and to a nitro group (1545 and 1370 cm$^{-1}$). GPC (solvent=tetrahydrofuran, temperature=40° C., in polystyrene equivalent) of this product gave a single peak, with $\overline{M}n=3.8\times10^4$ and $\overline{M}w=8.8\times10^4$. The elemental analysis data were: C 58.89%, H 7.94% and N 0.29% and, based on these data, the content of the spiropyran unit of general formula (I-2) in this polymer was identified as 1.1 mole percent.

A 10-mg portion of this polymer was dissolved in 2 ml of benzene and the solution was cast onto a quartz plate to give a purple film. This film initially had an absorption maximum at 540 nm but, after visible light irradiation using a 500-W ultrahigh pressure mercury lamp equipped with a cut-off filter allowing passage of visible rays of 500 nm and longer, the previous maximum absorption peak disappeared and the film became colorless and transparent. At room temperature (25° C.), this colorless film gradually became a purple color but did not become completely colored. It was stably fixed in and maintained a semi-uncolored state at an uncolored species fixation percentage of 76%.

Thus, upon ultraviolet irradiation, this film turned into the colored species and, upon visible light irradiation, shifted to the colorless state (uncolored species). When subsequently allowed to stand at 25° C., it maintained the semi-uncolored state at an uncolored species fixation percentage of 76%. This cycle could be repeated.

What is claimed is:

1. A macromolecular spiropyran compound which comprises 0.001 to 100 mole percent of a structural unit of the general formula

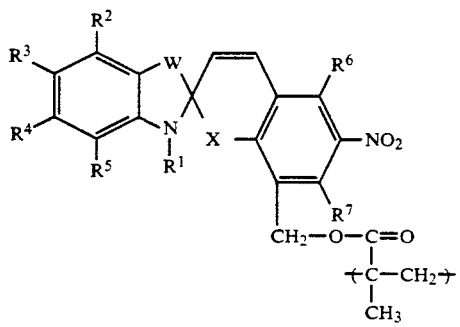

(I)

wherein W is

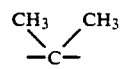

or —Se—, $R^1$ is an alkyl group containing 1 to 20 carbon atoms or an aralkyl group, $R^2$, $R^3$, $R^4$ and $R^5$ are the same or different and each represents a hydrogen atom, an alkyl group containing 1 to 6 carbon atoms, an aryl group, an aralkyl group, an alkoxy group containing 1 to 5 carbon atoms, a halogen atom, a cyano group, a trichloromethyl group, a trifluoromethyl group or a nitro group, $R^6$ and $R^7$ are the same or different and each represents a hydrogen atom, an alkyl group containing 1 to 6 carbon atoms, an aryl group, an aralkyl group, a halogen atom, a cyano group or a nitro group, and X is an oxygen or sulfur atom, with the proviso that X is a sulfur atom when W is

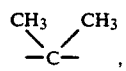

and (b) 0 to 99.999 mole percent of a structural unit of the general formula

(II)

wherein Y is a hydrogen atom or a methyl group and Z is a carboxyl group, an alkoxycarbonyl group, a cyano group, carbamoyl, an N,N-dimethylcarbamoyl group, an acetoxy group, a phenyl group or a methylphenyl group.

2. A compound as claimed in claim 1 which comprises 0.001 to 100 mole percent of a structural unit of the general formula

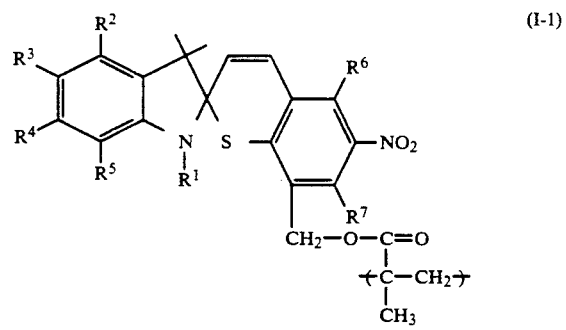

(I-1)

wherein $R^1$, $R^2$, $R^3$, $R^4$, $R^5$, $R^6$ and $R^7$ are as defined in claim 1, and 0 to 99.999 mole percent of a structural unit of the general formula

(II)

wherein Y and Z are as defined in claim 1.

3. A compound as claimed in claim 2 which has a number average molecular weight of about $5\times10^3$ to about $3\times10^5$ as determined by gel permeation chromatography (GPC) (solvent=tetrahydrofuran, temperature=40° C., in polystyrene equivalent) and a weight average molecular weight of about $5 \times 10^3$ to $5 \times 10^5$ as determined by the same GPC as mentioned above.

4. A compound as claimed in claim 2 which is a homopolymer consisting of the structural unit of general formula (I-1) alone.

5. A compound as claimed in claim 2 which comprises about 0.001 to about 50 mole percent of the structural unit of general formula (I-1) and about 50 to about 99.999 mole percent of the structural unit of general formula (II).

6. A compound as claimed in claim 2 which comprises about 0.01 to about 25 mole percent of the structural unit of general formula (I-1) and about 75 to about 99.99 mole percent of the structural unit of general formula (II).

7. A compound as claimed in claim 2 which comprises about 0.1 to about 10 mole percent of the structural unit of general formula (I-1) and about 90 to 99.9 mole percent of the structural unit of general formula (II).

8. A compound as claimed in claim 2, wherein, in general formula (I-1), $R^1$ is an alkyl group containing 1 to 20 carbon atoms, $R^2$, $R^3$, $R^4$ and $R^5$ are the same or different and each represents a hydrogen atom, a methyl group, an ethyl group, a phenyl group, a methoxyphenyl group, a methoxy group, an ethoxy group, a fluorine atom, a chlorine atom, a bromine atom, a cyano group or a nitro group, and $R^6$ and $R^7$ are the same or different and each represents a hydrogen atom, a methyl group, an ethyl group, a phenyl group or a naphthyl group.

9. A compound as claimed in claim 2, wherein, in general formula (I-1), $R^1$ is an alkyl group containing 1 to 20 carbon atoms, $R^2$, $R^3$, $R^4$ and $R^5$ are the same or different and each represents a hydrogen atom, a phenyl group, a methoxy group, a chlorine atom, a bromine atom, a cyano group or a nitro group, and $R^6$ and $R^7$ are the same or different and each represents a hydrogen atom, a phenyl group or a naphthyl group.

10. A compound as claimed in claim 2, wherein, in general formula (I-1), $R^1$ is an alkyl group containing 1 to 18 carbon atoms and $R^2$, $R^3$, $R^4$, $R^5$, $R^6$ and $R^7$ each is a hydrogen atom.

11. A compound as claimed in claim 2, wherein, in general formula (II), Y is a methyl group and Z is a methoxycarbonyl group, or Y is a hydrogen atom and Z is a phenyl group.

12. A compound as claimed in claim 2, wherein, in general formula (II), Y is a methyl group and Z is a methoxycarbonyl group.

13. A compound as claimed in claim 2, wherein, in general formula (II), Y is a hydrogen atom and Z is a phenyl group.

14. A compound as claimed in claim 1 which has a number average molecular weight of about $1 \times 10^3$ to about $1 \times 10^6$ as determined by gel permeation chromatography (GPC) (solvent=tetrahydrofuran, temperature=40° C., in polystyrene equivalent) and a weight average molecular weight of about $1 \times 10^3$ to about $1 \times 10^6$ as determined by the same GPC as mentioned above.

15. A compound as claimed in claim 1 which comprises 0.001 to 100 mole percent of a structural unit of the general formula

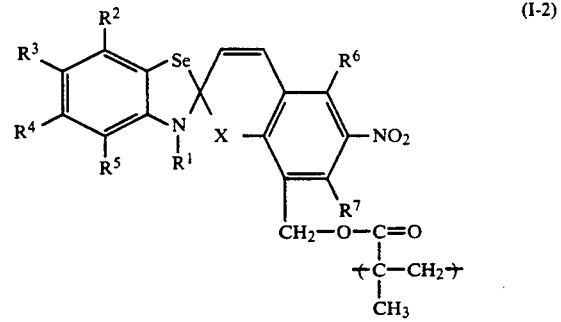

wherein $R^1$, $R^2$, $R^3$, $R^4$, $R^5$, $R^6$, $R^7$ and X are as defined in claim 1, and 0 to 99.999 mole percent of a structural unit of the general formula

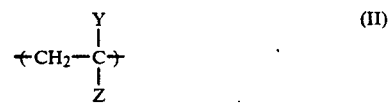

wherein Y and Z are as defined in claim 1.

16. A compound as claimed in claim 15 which has a number average molecular weight of about $1 \times 10^3$ to about $1 \times 10^6$ as determined by gel permeation chromatography (GPC) (solvent=tetrahydrofuran, temperature=40° C., in polystyrene equivalent) and a weight average molecular weight of about $1 \times 10^3$ to about $2 \times 10^6$ as determined by the same GPC mentioned above.

17. A compound as claimed in claim 15 which has a number average molecular weight of about $5 \times 10^3$ to about $3 \times 10^5$ as determined by gel permeation chromatography (GPC) (solvent=tetrahydrofuran, temperature=40° C., in polystyrene equivalent) and a weight average molecular weight of about $5 \times 10^3$ to about $5 \times 10^5$ as determined by the same GPC mentioned above.

18. A compound as claimed in claim 15 which is a homopolymer consisting of the structural unit of general formula (I-2) alone.

19. A compound as claimed in claim 15 which comprises about 0.001 to about 50 mole percent of the structural unit of general formula (I-2) and about 50 to about 99.999 mole percent of the structural unit of general formula (II).

20. A compound as claimed in claim 15 which comprises about 0.01 to about 25 mole percent of the structural unit of general formula (I-2) and about 75 to about 99.99 mole percent of the structural unit of general formula (II).

21. A compound as claimed in claim 15 which comprises about 0.1 to about 10 mole percent of the structural unit of general formula (I-2) and about 90 to about 99.9 mole percent of the structural unit of general formula (II).

22. A compound as claimed in claim 15, wherein, in general formula (I-2), $R^1$ is an alkyl group containing 1 to 20 carbon atoms, $R^2$, $R^3$, $R^4$ and $R^5$ are the same or different and each represents a hydrogen atom, a methyl group, an ethyl group, a phenyl group, a methoxyphenyl group, a methoxy group, an ethoxy group, a fluorine atom, a chlorine atom, a bromine atom, a cyano group or a nitro group, and $R^6$ and $R^7$ are the same or different and each represents a hydrogen atom, a methyl group, an ethyl group, a phenyl group or a naphthyl group.

23. A compound as claimed in claim 15, wherein, in general formula (I-2), $R^1$ is an alkyl group containing 1 to 20 carbon atoms, $R^2$, $R^3$, $R^4$ and $R^5$ are the same or different and each represents a hydrogen atom, a phenyl group, a methoxy group, a chlorine atom, a bromine atom, a cyano group or a nitro group, and $R^6$ and $R^7$ are the same or different and each is a hydrogen atom, a phenyl group or a naphthyl group.

24. A compound as claimed in claim 15, wherein, in general formula (I-2), $R^1$ is an alkyl group containing 1 to 20 carbon atoms, $R^2$ and $R^5$ each is a hydrogen atom, $R^3$ is a hydrogen atom or an alkoxy group containing 1 to 5 carbon atoms, $R^4$ is a hydrogen atom, an alkoxy group containing 1 to 5 carbon atoms or an alkyl group containing 1 to 6 carbon atoms, and X is an oxygen atom.

25. A compound as claimed in claim 15, wherein, in general formula (I-2), $R^1$ is a methyl group or an octadecyl group, $R^2$, $R^3$, $R^5$, $R^6$ and $R^7$ each is a hydrogen atom, $R^4$ is a hydrogen atom, a methyl group or a methoxy group, and X is an oxygen atom.

26. A compound as claimed in claim 15, wherein, in general formula (II), Y is a methyl group and Z is a methoxycarbonyl group, or X is a hydrogen atom and Z is a phenyl group.

27. A compound as claimed in claim 15, wherein, in general formula (II), Y is a methyl group and Z is a methoxycarbonyl group.

28. A compound as claimed in claim 15, wherein, in general formula (II), Y is a hydrogen atom and Z is a phenyl group.

* * * * *